(12) United States Patent
Ellington et al.

(10) Patent No.: US 6,429,298 B1
(45) Date of Patent: Aug. 6, 2002

(54) ASSAYS FOR IDENTIFYING FUNCTIONAL ALTERATIONS IN THE P53 TUMOR SUPPRESSOR

(75) Inventors: Andrew D. Ellington; Ichiro Matsumura, both of Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/417,278

(22) Filed: Oct. 13, 1999

Related U.S. Application Data
(60) Provisional application No. 60/103,930, filed on Oct. 13, 1998.

(51) Int. Cl.[7] .................. C07H 21/02; C12N 15/00; C07K 1/00; A61K 45/00; A61K 39/00
(52) U.S. Cl. ................ 536/23.1; 435/440; 530/300; 530/350; 424/278.1; 424/69.1; 424/277.1
(58) Field of Search ............... 435/440; 536/23.1; 530/300, 350; 424/278.1, 69.1

(56) References Cited

U.S. PATENT DOCUMENTS

| | | | |
|---|---|---|---|
| 4,888,286 A | 12/1989 | Crea | .......... 435/172.3 |

FOREIGN PATENT DOCUMENTS

| | | |
|---|---|---|
| EP | 0273085 | 12/1986 |
| EP | 0 518 650 A2 | 12/1992 |
| WO | WO 94/12202 | 6/1994 |
| WO | WO 95/06661 | 3/1995 |
| WO | WO 95/17213 | 6/1995 |
| WO | WO 95/19367 | 7/1995 |
| WO | WO 96/20207 | 7/1996 |
| WO | WO 97/10843 | 3/1997 |
| WO | WO 97/14794 | 4/1997 |

OTHER PUBLICATIONS

Gerbes and Casselmann, Point mutations of the p53 gene, human hepatocellular carcinoma and aflatoxins, Journal of Hepatology, 1993, 19; 312–315.*

Cadwell and Joyce, "Randomization of genes by PCR Mutagenesis," *PCR Methods Appl.*, 2(1):28–33, 1992.

Funk et al., "A transcriptionally active DNA–binding site for human p53 protein complexes," *Mol. Cell Biol.*, 12:2866–2871, 1992.

Hansen et al., "Allosteric regulation of the thermostability and DNA binding activity of human p53 by specific interacting proteins," *J. Biol. Chem.*, 271(7):3917–3924, 1996.

Hollstein et al., "p53 mutations in human cancers," *Science*, 253:49–53, 1991.

Hupp and Lane, "Allosteric activation of latent p53 tertramers," *Curr Biol.*, 4(10):865–875, 1994.

Hupp et al., "Regulation of the specific DNA binding function of p53," *Cell.*, 71(5):875–886, 1992.

Hupp and Lane, "Two distinct signaling pathways activate the latent DNA binding function of p53 in a casein kinase II–independent manner," *J Biol Chem.*, 270(30): 18165–18174, 1995.

(List continued on next page.)

*Primary Examiner*—Hankyel T. Park
*Assistant Examiner*—Stacy S. Brown
(74) *Attorney, Agent, or Firm*—Fulbright & Jaworski, LLP

(57) ABSTRACT

The present invention provides for various screening assays which are amenable to high throughput formats and identify a variety of useful mutations in tumor suppressor genes such as p53. Such mutations include those that activate the molecule, increase thermostability, increase transcriptional activity and facilitate resistance to inhibitory molecules. Also provided are methods of screening for accessory proteins that interact with tumor suppressors in both inhibitory and activating fashions, as well as cleavable mutants of p53 that are activated by viral proteases.

19 Claims, 9 Drawing Sheets

OTHER PUBLICATIONS

Hupp et al., "Small peptides activate the latent sequence-specific DNA binding function of p53," *Cell.*, 83(2):237–245, 1995.

Stemmer, "DNA shuffling by random fragmentation and reassembly: in vitro recombination for molecular evolution," *Proc. Nat'l Acad. Sci. USA*, 94:10747–10751, 1994.

Weinberg, "Tumor suppressor genes," *Science*, 254:1138–1145, 1991.

Hansen et al., "Allosteric regulation of the thermostabilty and dna binding activity of human p53 by specific interacting proteins," *J. Biol Chem*, 271:3917–3924, 1996.

Hansen et al., "Modification of two distinct cooh–terminal domains is required for murine p53 activation by bacterial hsp70", *J Biol Chem*, 271:30922–30928, 1996.

Matsumura et al., "In vitro evolution of thermostable p53 variants," *Protein Science*, 8:731–740, 1999.

Xirodimas and Lane, "Molecular evolution of the thermosensitive PAb1620 epitope of human p53 by dna shuffling," *J Biol Chem.*, 274:28042–28049, 1999.

* cited by examiner

ASSAYS FOR IDENTIFYING FUNCTIONAL ALTERATIONS IN THE P53 TUMOR SUPPRESSOR

This application claims priority to U.S. Provisional Application Ser. No. 60/103,930, filed on Oct. 13, 1998.

The government may own rights in the present invention. This work was supported by the Office of Naval Research, (N000149610341), and one of the inventors was supported in part by a National Science Foundation/Alfred P. Sloan Postdoctoral Research Fellowship in Molecular Evolution (DBI-9750002).

BACKGROUND OF THE INVENTION

1. Field of the Invention

The present invention relates generally to the fields of molecular biology and genetics. More particularly, it concerns the various functions of the p53 tumor suppressors and methods for identifying useful mutants having altered p53 function.

2. Description of Related Art p53, first thought to be an oncogene, is now the most widely recognized of the class of proteins known as tumor suppressors. Its complex involvement with gene transcription, genomic stability, chromosomal segregation, senescence, cell cycle regulation and apoptosis make it one of the most important regulatory molecules now known.

Mutations in p53 have been found in cells transformed by chemical carcinogenesis, ultraviolet radiation, and several viruses. The p53 gene is a frequent target of mutational inactivation in a wide variety of human tumors and is already documented to be the most frequently mutated gene in common human cancers. It is mutated in over 50% of human NSCLC (Hollstein et al., 1991) and in a wide spectrum of other tumors.

Although the specific molecular pathway(s) through which p53 responds to DNA damage are not known, it is well known that p53 binds to DNA in a sequence specific fashion. In addition, there is considerable evidence that p53 transactivates a number of important regulatory genes including p21$^{waf1}$, a potent inhibitor or most cycling-dependent kinases. Other gene products upon which p53 has some effect are GADD45, Bax, Fas, TBP, RPA, XPB, XPD and CSB.

The number of p53 molecules in a cell is limited, estimated at between $10^3$ and $10^4$ per cell. This relatively small number of molecules suggests some kind of post-translational regulation. One type of regulation is thought to be a reversible serine phosphorylation by at least seven distinct kinases including cdc2, casein kinase II, DNA-dependent protein kinase I, a casein kinase I-like kinase, protein kinase C, mitogen-activated kinase and JNK1. Though the precise role these different kinases play in phosphorylating p53 is not completely understood, a better understanding of the mechanisms is evolving. For example, a mutation in the casein kinase II phosphorylation site at serine 392 can reduce the antiproliferative activity of p53. Sequence specific DNA binding to p21$^{waf1}$ is stimulated by phosphorylation of the serine at 315.

One of the primary goals for researchers in the p53 field has been to develop a cancer gene therapy that relies on the replacement of defective p53 genes with a wild-type p53 gene. Several clinical trials have been approved utilizing viral vectors to deliver the p53 gene and have shown notable success. Possible limitations on therapies include the amount of viral vector that is administered, duration of expression, as well as the amount of p53 being expressed in the cells. Repeated administrations also raise concerns about vector toxicity and immunogenicity.

Thus, despite the growing amount of information on p53 function, and mounting evidence of its utility in gene therapy for cancer and other hyperproliferative diseases, there remains a need for improved compositions and techniques to fully exploit p53's remarkable biological activity.

SUMMARY OF THE INVENTION

Thus, according to the present invention, there are provided methods for identifying various modified forms of the tumor suppressor p53. In a first embodiment, there is provided a method of identifying a thermostable p53 polypeptide comprising providing a population of polynucleotides encoding activated, mutated p53 polypeptides; transforming host cells lacking an endogenous p53 polypeptide with said population of polynucleotides and culturing said host cells at elevated temperatures and under other conditions permitting the expression of said mutated, activated p53 polypeptides; screening said mutated p53 polypeptides for p53 DNA binding activity; and comparing the measured DNA binding with the DNA binding of an activated p53 polypeptide produced at said elevated temperatures, wherein increased binding of said activated, mutated p53 polypeptide, as compared to an activated p53 polypeptide, identifies a thermostable p53 polypeptide.

The method may further comprise the step of generating said population by creating random mutations in polynucleotides encoding an activated p53 polypeptide. The random mutations may be created by chemical mutagenesis, PCR mutagenesis, RT hypermutagenesis or DNA shuffling. In a particular embodiment, the activated p53 polypeptide contains a truncation of a C-terminal portion of wild-type p53, for example the 30 C-terminal amino acid residues. Alternatively, the truncation may specifically encompass residue 360, or one or more point mutations when compared to wild-type p53. In another embodiment, the activated p53 molecule may contain an insertion as compared to wild-type p53, or a substitution in the C-terminus of wild-type p53. In yet another embodiment, the activated p53 polypeptide comprises an internal deletion.

The host cells may be bacterial cells, for example, *Escherichia coli*. Alternatively, the host cells may be eukaryotic cells, for example, yeast cells. The binding activity may be determined using a labeled target DNA, for example, where label is a radiolabel, a chemilluminescent label or a fluorescent label. The elevated temperature may be 37° C.

Also provided are thermostable p53 polypeptides comprising a first point mutation. Throughout the application, reference to a particular residues of p53 is made by reference to SEQ ID NO:2. The first point mutation may be Val$^{133}$, Tyr$^{239}$, Asp$^{268}$, Val$^{336}$, Pro$^{364}$, Val$^{62}$, Thr$^{116}$ Pro$^{166}$, Th$^{270}$, Ser$^{88}$, Ile$^{157}$, Val$^{344}$, Gly$^{42}$, Ser$^{268}$, Lys$^{51}$, Gly$^{326}$, Glu$^{207}$, Ser$^{212}$, His$^{264}$, Ala$^{203}$, Leu$^{80}$, Ala$^{30}$, Lys$^{56}$, Asn$^{106}$, Arg$^{115}$, Ser$^{277}$, Met$^{344}$, Gln$^{45}$, Ala$^{102}$, Ser$^{191}$, Thr$^{322}$, Ala$^{31}$, Gly$^{49}$, Thr$^{183}$, Ile$^{264}$ or Val$^{346}$. The polypeptide may further comprise a second point mutation. The combinations may be where said first point mutation is Gly$^{42}$ and said second point mutation is Ser$^{268}$, where said first point mutation is Lys$^{51}$ and said second point mutation is Gly$^{326}$, where said first point mutation is Leu$^{80}$ and said second point mutation is Ala$^{203}$, where said first point mutation is Ser$^{277}$ and said second point mutation is Met$^{344}$.

The polypeptide may further comprise a third point mutation. The combinations may be where said first point mutation is Tyr$^{239}$, said second point mutation is Asp$^{269}$, and said third point mutation is Val$^{336}$; where said first point mutation is Val$^{62}$, said second point mutation is Tyr$^{239}$, and said third point mutation is Asp$^{268}$; where said first point mutation is Asp$^{268}$, said second point mutation is Val$^{336}$, and said third point mutation is Pro$^{364}$; where said first point mutation is Ser$^{88}$, said second point mutation is Ile$^{157}$, and said third point mutation is Val$^{344}$; or where said first point mutation is Glu$^{207}$, said second point mutation is Ser$^{212}$, and said third point mutation is His$^{364}$. The polypeptide may further comprise a fourth point mutation. The combinations may be where said first point mutation is Thr$^{116}$, said second point mutation is Pro$^{166}$, said third point mutation is Asp$^{268}$, and said fourth point mutation is Thr$^{270}$.

The polypeptide may further comprise a fifth point mutation. The combinations may be where said first point mutation is Val$^{133}$, said second point mutation is Tyr$^{239}$, said third point mutation is Asp$^{268}$, said fourth point mutation is Val$^{336}$, and said fifth point mutation is Pro$^{364}$; where said first point mutation is Ala$^{30}$, said second point mutation is Lys$^{56}$, said third point mutation is Asn$^{106}$, said fourth point mutation is Arg$^{115}$, and said fifth point mutation is Ala$^{203}$; where said first point mutation is Gln$^{45}$, said second point mutation is Ala$^{102}$, said third point mutation is Ser$^{191}$, said fourth point mutation is Glu$^{207}$, and said fifth point mutation is Thr$^{332}$; or where said first point mutation is Ala$^{31}$, said second point mutation is Gly$^{49}$, said third point mutation is Thr$^{183}$, said fourth point mutation is Ile$^{264}$, and said fifth point mutation is Val$^{346}$.

In another embodiment, there is provided a method of identifying an activated p53 polypeptide comprising providing a population of polynucleotides encoding mutated p53 polypeptides; transforming bacterial host cells lacking an endogenous p53 polypeptide with said population of polynucleotides and culturing said host cells under conditions permitting the expression of said mutated p53 polypeptides; screening said mutated p53 polypeptides for p53 DNA binding activity; and comparing the measured DNA binding of step with the DNA binding of wild-type p53, wherein increased binding of a mutated p53 polypeptide, as compared to wild-type p53, identifies an activated p53 polypeptide.

The method may further comprise the step of generating said population by creating random mutations in polynucleotides encoding wild-type p53, for example, by chemical mutagenesis, PCR mutagenesis, RT hypermutagenesis or DNA shuffling.

Again, the bacterial host cells may be *Escherichia coli*. The screening for DNA binding activity may comprise lysing said host cells and contacting the lysates with a target DNA to which activated p53 binds. The target DNA may be labeled.

In yet another embodiment, there is provided an activated p53 polypeptide. The polypeptide may comprise a deletion of residue 360, but retain sequences flanking residues 360. Alternatively, the polypeptide may comprise a first point mutation when compared to wild-type p53, such as Lys$^3$, Arg$^{23}$, Ser$^{54}$, Asn$^{106}$, Ala$^{123}$, Arg$^{137}$, Thr$^{159}$, Thr$^{160}$, Asp$^{268}$, Ser$^{268}$, Thr$^{332}$, Gly$^{339}$ or Val$^{344}$. The polypeptide may comprise a second point mutation. The combinations may be where said first point mutation is Leu$^{77}$ and said second point mutation is Ala$^{122}$. The polypeptide may comprise a third point mutation. The combinations may be wherein said first point mutation is Leu$^4$, said second point mutation is Ala$^{225}$, and said third point mutation is Ser$^{310}$. Alternatively, the polypeptide may comprise an insertion when compared to wild-type p53, for example, an insertion at residue 360. The polypeptide may also comprise, in addition to an insertion, an internal deletion, such as, where said insertion is at residue 317 and said deletion is at residue 365.

In still yet another embodiment, there is provided a method of identifying an activator of p53 DNA binding comprising providing a plurality of cDNAs and a polynucleotide encoding a full length p53 polypeptide; transforming host cells lacking an endogenous p53 polypeptide with said cDNAs and said p53-encoding polynucleotide, and culturing said host cells under conditions permitting the expression of products encoded by said cDNAs and said full length p53 polypeptide; and screening said products encoded by said cDNAs for p53 DNA binding activity.

In yet a further embodiment, there is provided a method of identifying an inhibitor of p53 DNA binding comprising providing a plurality of cDNAs and a polynucleotide encoding an activated p53 polypeptide; transforming host cells lacking an endogenous p53 polypeptide with said cDNAs and said p53-encoding polynucleotide, and culturing said host cells under conditions permitting the expression of products encoded by said cDNAs and said activated p53 polypeptide; and screening said products encoded by said cDNAs for loss of p53 DNA binding activity.

In still yet a different embodiment, there is provided a method of identifying SV40 resistant p53 polypeptides comprising providing a polynucleotide encoding the SV40 large T antigen and a population of polynucleotides encoding mutated, activated p53 polypeptides; transforming host cells lacking an endogenous p53 polypeptide with said SV40 large T antigen-encoding polynucleotide and said p53-encoding polynucleotides, and culturing said host cells under conditions permitting the expression of said SV40 large T antigen and said mutated, activated p53 polypeptides; screening said mutated, activated p53 polypeptides for p53 DNA binding activity; and comparing the measured DNA binding with the DNA of an activated p53 polypeptide coexpressed with SV40 large T antigen, wherein increased binding of a mutated, activated p53 polypeptide, as compared to activated p53, identifies an SV40 resistant p53 polypeptide.

In another embodiment, there is provided a method for identifying a p53 polypeptide with increased transcriptional activity comprising providing a population of mutated p53 polypeptides; transforming host cells lacking an endogenous p53 polypeptide with said population of mutated p53 molecules, wherein said host cells contain a reporter gene driven by a p53-dependent promoter; screening said host cells for expression of the gene product encoded by said reporter gene; and comparing the measured expression of said reporter gene with the expression of said reporter gene by wild-type p53, wherein an increase in the expression of said reporter gene in cells expressing said mutated p53 molecules, as compared to cells expressing wild-type p53, indicates a p53 polypeptide having increased transcriptional activity.

The reporter gene may encode a fluorescent polypeptide and said screening comprises fluorescence activated cell sorting. The host cells may be osteocarcinoma cells and said transforming may comprise retroviral infection with a population of retroviruses encoding said mutated p53 polypeptides. The method may further comprise the step of PCR amplification of an identified p53 polypeptide having increased transcriptional activity.

In yet a different embodiment, there is provided a mutant p53 polypeptide containing an HIV-1 protease cleavage site upstream of the carboxy-terminal region thereof, whereupon cleavage by HIV-1 protease, said p53 molecule is activated. The polypeptide may comprise all of the wild-type p53 residues in addition to said protease cleavage site, or the cleavage site may replace a similar sized region of the wild-type p53 polypeptide. The cleavage site, in a particular embodiment, is VSFNFPQITL. The cleavage site may be inserted immediately after amino acid residue 359. The amino acid sequence VSFNFPQITL may be substituted for amino acid residues 360–369 of the wild-type p53 amino acid sequence.

Another aspect of the invention is an infectious retrovirus, the RNA of which encodes a mutant p53 polypeptide containing an HIV-1 protease cleavage site upstream of the carboxy-terminal region thereof, whereupon cleavage by HIV-1 protease, said p53 molecule is activated. Preferably, the mutant p53 coding region is under the control of the viral LTR.

Still another aspect of the invention is a method of inhibiting HIV-1 replication in a cell infected with HIV-1 comprising contacting said cell with an infectious retrovirus, the RNA of which encodes a mutant p53 polypeptide containing an HIV-1 Tat protease cleavage site upstream of the carboxy-terminal region thereof, whereupon cleavage by HIV-1 Tat, said p53 molecule is activated. The method may further comprise treatment of said cell with AZT or with HAART.

Still yet another aspect of the invention is a polynucleotide encoding a thermostable p53 polypeptide comprising a first point mutation selected from the group consisting of $Val^{133}$, $Tyr^{239}$, $Asp^{268}$, $Val^{336}$, $Pro^{364}$, $Val^{62}$, $Thr^{116}$, $Pro^{166}$, $Thr^{270}$, $Ser^{88}$, $Ile^{157}$, $Val^{344}$, $Gly^{42}$, $Ser^{268}$, $Lys^{51}$, $Gly^{326}$, $Glu^{207}$, $Ser^{212}$, $His^{264}$, $Ala^{203}$, $Leu^{80}$, $Ala^{30}$, $Lys^{53}$, $Asn^{106}$, $Arg^{115}$, $Ser^{277}$, $Met^{344}$, $Gln^{45}$, $Ala^{102}$, $Ser^{191}$, $Thr^{322}$, $Ala^{31}$, $Gly^{49}$, $Thr^{183}$, $Ile^{264}$, and $Val^{346}$. Another polynucleotide according to the invention encodes an activated p53 polypeptide comprising of a deletion of residue 360, but retaining sequences flanking residues 360. Still another polynucleotide according to the invention encodes an activated p53 polypeptide comprising a first point mutation when compared to wild-type p53. Still yet another polynucleotide of the invention encodes an activated p53 polypeptide comprising an insertion when compared to wild-type p53, and further may comprise a deletion.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A: Binding of mutated p53 DNA molecules with radiolabeled target DNA binding site, as compared to various controls (no p53, wild-type p53, activated p53). FIG. 2B: Map showing location of single mutants.

DESCRIPTION OF ILLUSTRATIVE EMBODIMENTS

Figure 1:
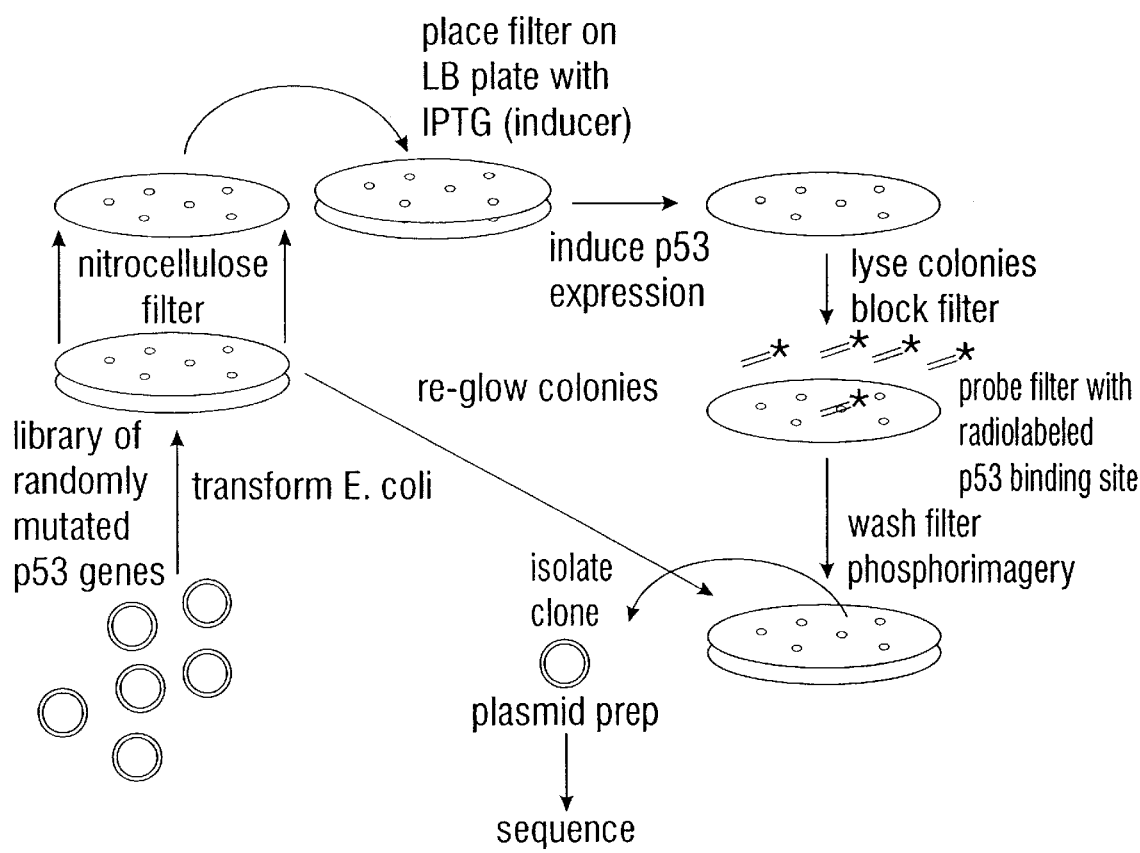
FIG. 1—Scheme for Selection of "Self-Activating" or Consitutively Active Mutants of p53.

As discussed above, p53 plays an essential role in the regulation of normal cell cycle and in the control of DNA damage. Considerable efforts have been expended in attempting to determine how this gene works and the extent to which it can be used in the diagnosis and therapy of hyperproliferative diseases such as cancer.

Regardless of previous successes, it is desirable to obtain new and improved versions of p53 which retain many of the protective and reparative aspects of this molecule while overcoming various of its limitations. Such new, "second generation" molecules may dramatically improve the current gene therapies based on p53.

I. The Present Invention

The present invention centers around various high throughput screening assays useful for selecting mutants of the p53 tumor suppressor. In addition, through the exploitation of these assays, various mutants having altered or improved characteristics have been identified.

In a first embodiment, an assay is provided for identifying mutants of p53 that are constitutively active. Normally, the carboxy-terminal 30 amino acids of the molecule act as an inhibitor of the DNA binding function until they are bound, phosphorylated or deleted. In this assay, large numbers of mutant polynucleotides are screened for the ability to produce polypeptides that overcome this C-terminal-mediated repression. A number of mutants in this class already have been identified.

In a second embodiment, using a slight modification of the assay described above, activated polynucleotides are further randomly mutagenized and screened for the ability to produce polypeptides that represent thermostable p53 molecules. By selecting those molecules that continue to bind after extended incubation at the physiological temperature, the inventors have identified several thermostable variants of p53.

Proteins that interact directly with p53 have been discovered one at a time by virtue of their affinities for p53. Unfortunately, proteins that bind transiently, such as those that catalyze covalent modification, cannot be identified in this way. Thus, in a third embodiment, the assay is further modified to screen for activators and inhibitors of p53 DNA binding. Here, using a polynucleotide encoding the full length p53 molecule, a cDNA library is screened for its ability to produce a factor that will activate the otherwise inactive p53 polypeptide. Any colony exhibiting DNA binding activity is isolated and the cDNA analyzed. Conversely, using a polynucleotide encoding an activated p53 molecule, inhibitory cDNA can be identified in colonies which lack DNA binding activity.

A number of viral and oncogenic proteins bind p53 and inhibit its DNA binding activity. This is a serious issue with respect to immortalization of virus-infected and cancerous cells. Thus, in a fourth embodiment, a mutagenized population of polynucleotides encoding activated p53 polypeptides will either be co-expressed or treated with exogenously added viral inhibitor proteins. If the resulting mutation abrogates the viral repression of DNA binding while retaining that activity, the mutant can be identified by DNA binding activity, thereby identifying the repressor resistant mutants.

One of the important activities possessed by p53 is the ability to activate certain genes, in a transcriptional fashion. Many of these activated genes participate directly or indirectly in cell cycle regulation and apoptosis. Thus, in a fifth embodiment, the assay is modified to look at the transcriptional promoting activity of p53. Randomly mutated p53 polynucleotides are screened for their ability to increase the transcription of a marker gene under the control of a p53-regulated promoter. Where the marker gene expresses a fluorescent protein, the cells can be sorted by FACS, increasing the speed and number of clones that can be identified.

II. p53 Polypeptides

A. p53 as a Tumor Suppressor

The p53 gene encodes a 393-amino acid phosphoprotein that can form complexes with host proteins such as large-T antigen and E1B. It acts primarily as a transcription factor to control the expression of proteins involved in the cell cycle. In response to DNA damage, p53 accumulates in the nucleus and arrests the cell cycle via the cyclin dependent kinase inhibitor p21 WAF1/CIP1. Alternatively, p53 can induce apoptosis or programmed cell death through both transcription-dependent and -independent pathways. p53 also is found in normal tissues and cells, but at much lower concentrations. Overexpression of wild-type p53 has been shown in some cases to be anti-proliferative in human tumor cell lines. Thus, p53 can act as a negative regulator of cell growth (Weinberg, 1991) and may directly suppress uncontrolled cell growth or indirectly activate genes that suppress this growth. Thus, absence or inactivation of wild-type p53 may contribute to transformation.

Wild-type p53 is recognized as an important growth regulator in many cell types. Missense mutations are common for the p53 gene in transformed cells. p53 point mutations are known to occur in hundreds of distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

A number of reports have demonstrated that DNA encoding wild-type p53 can restore growth suppression in tumor cells. p53 appears dominant over the mutant gene and will select against proliferation when transfected into cells with the mutant gene. Normal expression of the transfected p53 does not affect the growth of cells with endogenous p53. Thus, such constructs are be taken up by normal cells without adverse effects. Numerous clinical trials have been conducted using the p53 in various different vectors, routes of administration and different tumors.

Though the present invention is exemplified with p53, other tumor suppressors, including p16, RB, APC, NF-1, WT-1, p73, and VHL, could be explored using the same approach. Each of these is known to bind a particular macromolecule target, which could be labeled and utilized as a probe in a functional screen. In the case of DNA binding tumor suppressors, one could screen for DNA binding. For others, binding to accessory proteins could be monitored.

B. Activated p53 Molecules

Wild-type p53 is known to bind to DNA through a sequence-specific mechanism. This activity is allosterically regulated, as the unmodified polypeptide is inactive until the C-terminal 30 amino acids are bound by antibody, phosphorylated or deleted (Hupp et al., 1992). A model has been formulated in which the unmodified C-terminal tail binds an unidentified peptide binding pocket and holds the p53 tetramer in an inactive conformation (Hupp et al., 1995).

The present invention contemplates the use of constitutively activated p53 molecules. These molecules are characterized by one or more mutations that release the p53 from the inactivating constraints of the molecule's C-terminus. Surprisingly, the mutations may occur throughout the p53 molecule and are not confined to those residing in the C-terminus.

Figure 2A:
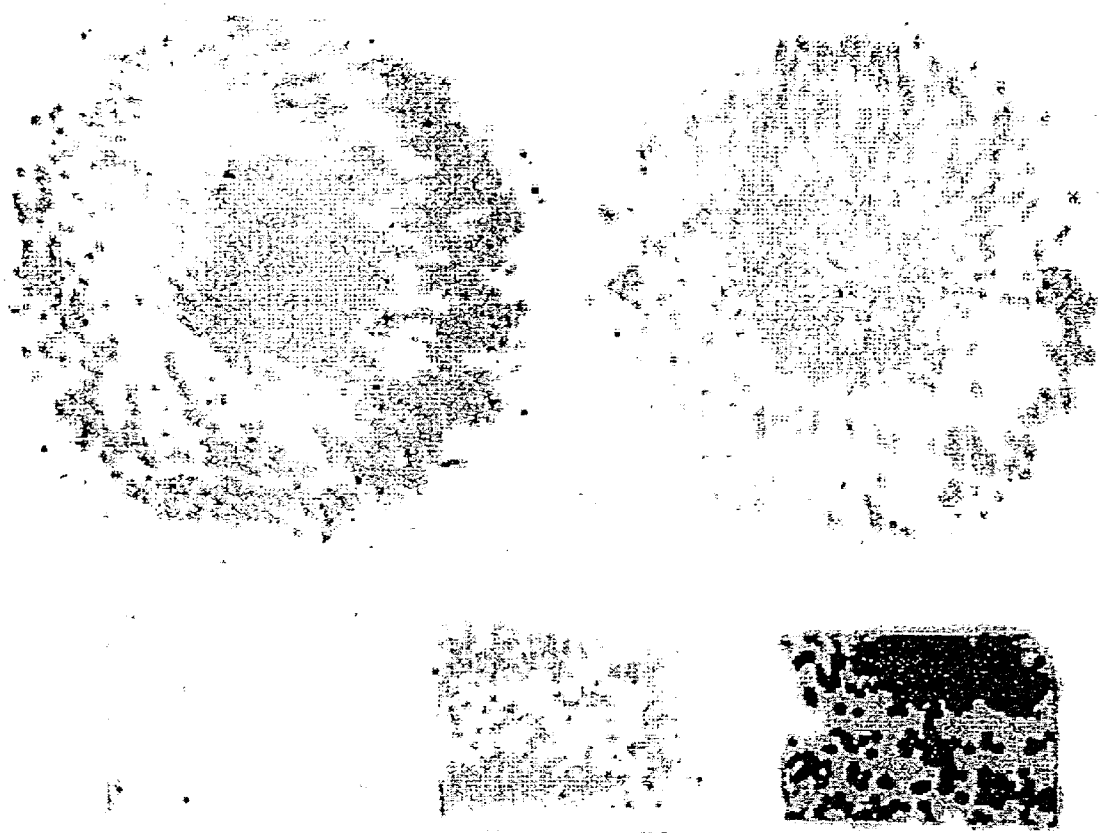
FIGS. 2A and 2B—Screening and Isolation of Self-Activating Mutants of p53.
Figure 2B:
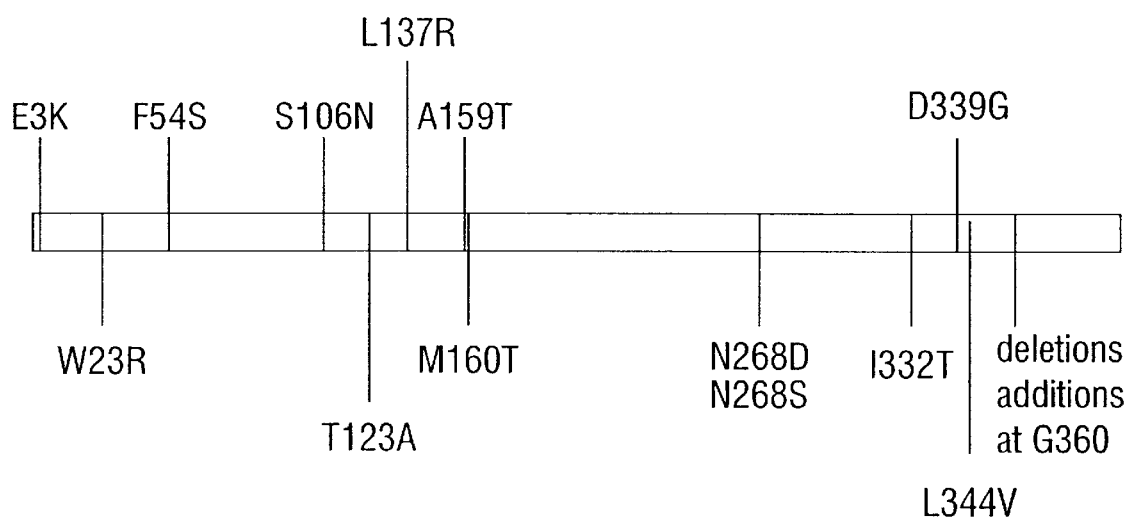

The full-length p53 cDNA was randomly mutated by mutagenic PCR™ (Cadwell and Joyce, 1992); the resulting library was screened for mutants with DNA binding activity greater than that of wild-type. The screens were similar to those described above, except that the inductions were carried out at room temperature (FIG. 2A). The mutants that were reproducibly more active than the wild-type were sequenced. The inferred amino acid changes occur over the whole gene (FIG. 2B). The mutations in the sequence specific DNA binding domain clustered in two areas in three dimensional space.

C. Thermostable p53 Molecules

Another p53 molecule identified in the present invention is a thermostable p53 molecule. The half-life of wild-type p53 is limited by its thermolability. These thermostable molecules are resistant to inactivation at physiological temperatures and, thus, will be useful in gene therapy applications where expression of an active gene product in vivo is desired. In various embodiments, the thermostable mutations may be combined with a mutation that confers constitutive activation.

Notably, for variants selected from the first and second rounds of screening, many of the sequence substitutions map to portions of the p53 structure that are not immediately adjacent to the DNA binding interface. These thermostable mutations would therefore have been difficult to discover by other means, such as site-directed mutagenesis or random mutation of a delimited region. The inventors are in the process of identifying additional variants that confer additional thermostabilities.

D. Viral Protease-Activated p53 Molecules

Still another type of p53 molecule, according to the present invention, is a cleavable p53 molecule, the cleaved product of which is constitutively activated. In particular, the present invention is directed to a p53 molecule that contains the protease cleavage site of the HIV-1 protease. By engineering the wild-type p53 gene to include, either by insertion or substitution, the HIV-1 protease cleavage site (VSFNFPQITL) at the appropriate location, it is possible to create a molecule that is selectively activated by HIV-1 protease. Because p53 represses the transcription of HIV-1 genes that are necessary for viral replication, this p53 molecule has therapeutic potential in the treatment of this disease.

As discussed above, the carboxy-terminal 30 amino acids of p53 act to repress the DNA-binding function of p53 until bound, phosphorylated or removed. Thus, insertion or substitution of a protease cleavage site at about 30 amino acids from the C-terminus should result, upon subsequent cleavage, of an activated p53 molecule. In a preferred embodiment, the 10 residue cleavage site is substituted for residues 360–369 of the wild-type p5$^3$ sequence.

E. Oncogene and Virus Resistant p53 Molecules

A number of viral and oncogenic polypeptides bind p53 and inhibit its activity. For example, the SV40 T antigen inhibits the DNA binding activity of p53. By selecting mutants of p53 that bind DNA in the presence of T antigen, mutant polypeptides that are resistant to the limiting effects of T antigen can be identified.

III. Polynucleotides, Expression Vectors and Cellular Transformation

A. Polynucleotides Encoding p53

Polynucleotides according to the present invention may encode an entire p53 gene, a domain of p53 that expresses a tumor suppressing or DNA binding function, or any other fragment of a p53 gene as set forth herein. Also included are polymorphic variants (such as the codon 72 variants Arg or Pro) that can be used to distinguish a one particular p53 product from another. The nucleic acid may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." At a minimum, these and other nucleic acids of the present invention may be used as standards in any screen to identify stabilizing mutations in human populations.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a given p53 gene from a given species may be represented by natural variants that have slightly different polynucleotide sequences but, nonetheless, encode the same protein (see Table 1 below).

As used in this application, the term "a polynucleotide encoding a p53" refers to a polynucleotide that has been isolated free of other cellular nucleic acids or synthesized from a p53 polynucleotide template. Various allelic forms of p53 exist, all of which exhibit "wild-type" activity—tumor suppression. The include NCBI 129369, and X54156 and M22881 from GenBank, The term "functionally equivalent codon" is used herein to refer to codons that encode the same amino acid, such as the six codons for arginine or serine (Table 1, below), and also refers to codons that encode biologically equivalent amino acids, as discussed in the following pages.

TABLE 1

| Amino Acids | | | Codons | | | | | |
|---|---|---|---|---|---|---|---|---|
| Alanine | Ala | A | GCA | GCC | GCG | GCT | | |
| Cysteine | Cys | C | TGC | TGT | | | | |
| Aspartic acid | Asp | D | GAC | GAT | | | | |
| Glutamic acid | Glu | E | GAA | GAG | | | | |
| Phenylalanine | Phe | F | TTC | TTT | | | | |
| Glycine | Gly | G | GGA | GGC | GGG | GGT | | |
| Histidine | His | H | CAC | CAT | | | | |
| Isoleucine | Ile | I | ATA | ATC | ATT | | | |
| Lysine | Lys | K | AAA | AAG | | | | |
| Leucine | Leu | L | TTA | TTG | CTA | CTC | CTG | CTT |
| Methionine | Met | M | ATG | | | | | |
| Asparagine | Asn | N | AAC | AAT | | | | |
| Proline | Pro | P | CCA | CCC | CCG | CCT | | |
| Glutamine | Gln | Q | CAA | CAG | | | | |
| Arginine | Arg | R | AGA | AGG | CGA | CGC | CGG | CGT |
| Serine | Ser | S | AGC | AGT | TCA | TCC | TCG | TCT |
| Threonine | Thr | T | ACA | ACC | ACG | ACT | | |
| Valine | Val | V | GTA | GTC | GTG | GTT | | |
| Tryptophan | Trp | W | TGG | | | | | |
| Tyrosine | Tyr | Y | TAC | TAT | | | | |

Figure 7:
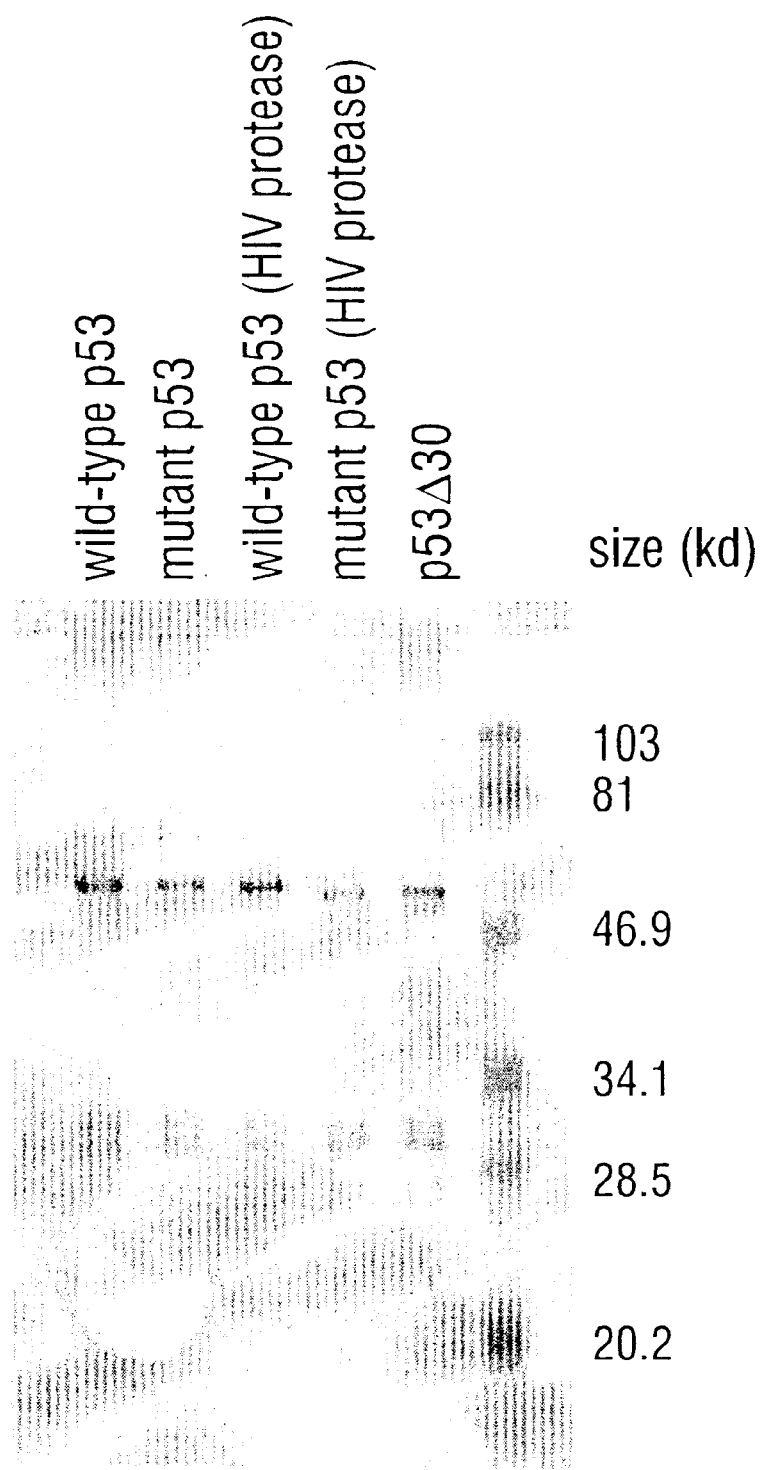
FIG. 7—HIV protease specifically truncates the engineered p53. Human p53 cDNA was engineered to contain the cleavage site for HIV protease, upstream of the carboxy-terminal 30 amino acids. The wild-type, p53Δ30 (pretruncated) and engineered variants were expressed as fusion proteins with amino terminal hexahistidine tags. The wild-type and mutant fusion proteins also were co-expressed with HIV protease. The proteins were purified on nickel chelating columns, and run on SDS-PAGE gels. The mutant p53 migrates slightly faster than wild-type proteins only after coexpression with HIV protease.
Figure 8:
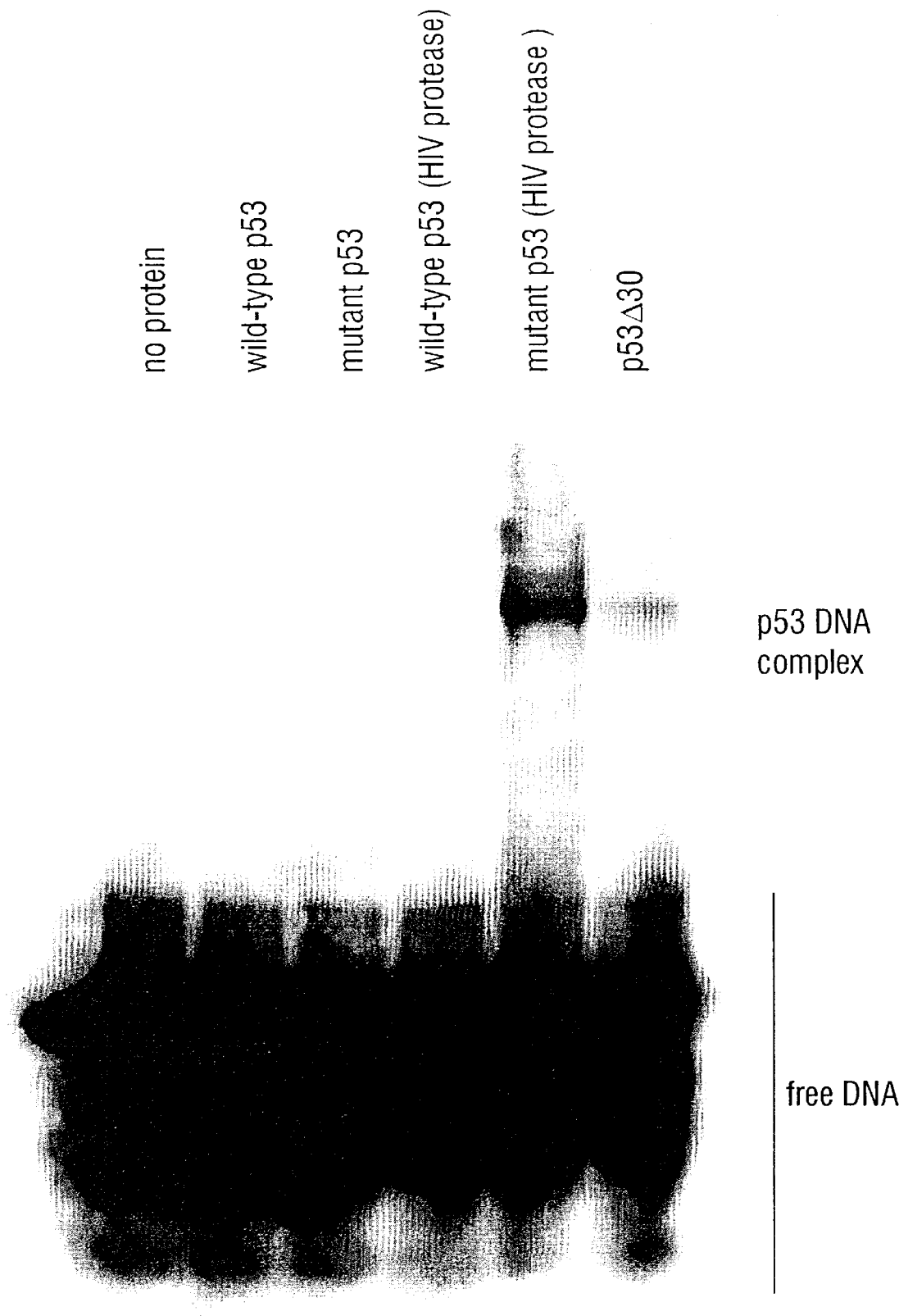
FIG. 8—HIV protease activates engineered p53. The p53 fusion proteins described in FIG. 7 were incubated with radiolabeled oligonucleotides encoding the p53 binding site of the p21 enhancer. The complexed and free oligonucleotides were separated on a non-denaturing gel. HIV protease dramatically enhances the DNA binding activity of the mutant p53, but not that of wild-type p53.

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of FIG. 7 will be sequences that are "as set forth in FIG. 7." Sequences that are essentially the same as those set forth in FIG. 7 also may be functionally defined as sequences that are capable of hybridizing to a nucleic acid segment containing the complement of FIG. 7 under standard conditions.

B. Oligonucteotide Probes and Primers

Naturally, the present invention also encompasses DNA segments that are complementary, or essentially complementary, to the sequence set forth in FIG. 7. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the polynucleotide of FIG. 7 under relatively stringent conditions such as those described herein. Such sequences may encode the entire p53 protein or functional or non-functional fragments thereof.

Alternatively, the hybridizing segments may be shorter oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 500, 1000, 1212, 1500, 2000, 2500, 3000 or 5000 bases and longer are contemplated as well. Such oligonucleotides will find use, for example, as probes in Southern and Northern blots and as primers in amplification reactions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 $\mu$M $MgCl_2$, at temperatures ranging from approximately 40° C. to about 72° C. Formamide and SDS also may be used to alter the hybridization conditions.

C. Methods of Mutagenizing Polynucleotides (i) Random Mutagenesis

As part of the present invention, it is desired that random single or multiple mutations be generated. Various methods for randomized mutagenesis are known in the field. For example, recombinant vectors encoding the desired gene may be treated with mutagenic agents, such as hydroxylamine, to obtain sequence variants. Alternatively, enzymatic methods may be involved, for example, with the use of high error rate polymerases. Cadwell & Joyce (1992).

(ii) Site-directed Mutagenesis

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique of site-specific mutagenesis is well known in the art. As will be appreciated, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants. Suitable techniques are also described in U.S. Pat. No. 4,888,286, incorporated herein by reference.

Although the foregoing methods are suitable for use in mutagenesis, the use of the polymerase chain reaction (PCR™) is generally now preferred. This technology offers a quick and efficient method for introducing desired mutations into a given DNA sequence. The following text particularly describes the use of PCR™ to introduce point mutations into a sequence, as may be used to change the amino acid encoded by the given sequence. Adaptations of this method are also suitable for introducing restriction enzyme sites into a DNA molecule.

In this method, synthetic oligonucleotides are designed to incorporate a point mutation at one end of an amplified segment. Following PCR™, the amplified fragments are blunt-ended by treating with Klenow fragments, and the blunt-ended fragments are then ligated and subcloned into a vector to facilitate sequence analysis.

To prepare the template DNA that one desires to mutagenize, the DNA is subcloned into a high copy number vector, such as pUC19, using restriction sites flanking the area to be mutated. Template DNA is then prepared using a plasmid miniprep. Appropriate oligonucleotide primers that are based upon the parent sequence, but which contain the desired point mutation and which are flanked at the 5' end by a restriction enzyme site, are synthesized using an automated synthesizer. It is generally required that the primer be homologous to the template DNA for about 15 bases or so. Primers may be purified by denaturing polyacrylamide gel electrophoresis, although this is not absolutely necessary for use in PCR™. The 5' end of the oligonucleotides should then be phosphorylated.

The template DNA should be amplified by PCR™, using the oligonucleotide primers that contain the desired point mutations. The concentration of $MgCl_2$ in the amplification buffer will generally be about 15 mM. Generally about 20–25 cycles of PCR™ should be carried out as follows: denaturation, 35 sec. at 95° C.; hybridization, 2 min. at 50° C.; and extension, 2 min. at 72° C. The PCR™ will generally include a last cycle extension of about 10 min. at 72° C. After the final extension step, about 5 units of Klenow fragments should be added to the reaction mixture and incubated for a further 15 min. at about 30° C. The exonuclease activity of the Klenow fragments is required to make the ends flush and suitable for blunt-end cloning.

The resultant reaction mixture should generally be analyzed by nondenaturing agarose or acrylamide gel electrophoresis to verify that the amplification has yielded the predicted product. One would then process the reaction mixture by removing most of the mineral oils, extracting with chloroform to remove the remaining oil, extracting with buffered phenol and then concentrating by precipitation with 100% ethanol. Next, one should digest about half of the amplified fragments with a restriction enzyme that cuts at the flanking sequences used in the oligonucleotides. The digested fragments are purified on a low gelling/melting agarose gel.

To subclone the fragments and to check the point mutation, one would subclone the two amplified fragments into an appropriately digested vector by blunt-end ligation. This would be used to transform *E. coli*, from which plasmid DNA could subsequently be prepared using a miniprep. The amplified portion of the plasmid DNA would then be analyzed by DNA sequencing to confirm that the correct point mutation was generated. This is important as Taq DNA polymerase can introduce additional mutations into DNA fragments.

The introduction of a point mutation can also be effected using sequential PCR™ steps. In this procedure, the two fragments encompassing the mutation are annealed with each other and extended by mutually primed synthesis. This fragment is then amplified by a second PCR™ step, thereby avoiding the blunt-end ligation required in the above protocol. In this method, the preparation of the template DNA, the generation of the oligonucleotide primers and the first PCR™ amplification are performed as described above. In this process, however, the chosen oligonucleotides should be homologous to the template DNA for a stretch of between about 15 and about 20 bases and must also overlap with each other by about 10 bases or more.

In the second PCR™ amplification, one would use each amplified fragment and each flanking sequence primer and carry PCR™ for between about 20 and about 25 cycles, using the conditions as described above. One would again subclone the fragments and check that the point mutation was correct by using the steps outlined above.

In using either of the foregoing methods, it is generally preferred to introduce the mutation by amplifying as small a fragment as possible. Of course, parameters such as the melting temperature of the oligonucleotide, as will generally be influenced by the GC content and the length of the oligo, should also be carefully considered. The execution of these methods, and their optimization if necessary, will be known to those of skill in the art, and are further described in various publications, such as *Current Protocols in Molecular Biology* (1995), incorporated herein by reference.

D. Vectors for Cloning, Gene Transfer and Expression

Within certain embodiments expression vectors are employed to express the p53 polypeptide product for screening. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™ 11 may be utilized in making a recombinant phage vector which can be used to transform host cells, such as *E. coli* LE392.

Further useful vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, the like.

Viral vectors are preferred eukaryotic expression systems. Included are adenoviruses, adeno-associated viruses, retroviruses, herpesviruses, poxviruses including vaccinia viruses and papilloma viruses including SV40.

(i) Regulatory Elements

Throughout this application, the term "expression construct" is meant to include any type of genetic construct containing a polynucleotide coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

In preferred embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

Prokaryotic promoters that are most commonly used in recombinant DNA construction include the lactose (lac), T7, β-lactamase (penicillinase), tryptophan (trp) and the composite tryptophan/lactose (tac) promoter systems. While these are the most commonly used, other microbial promoters have been discovered and utilized, and details concerning their nucleotide sequences have been published, enabling those of skill in the art to ligate them functionally with plasmid vectors. Particularly preferred is the pET System (Novagen Corp., Madison, Wis.).

The term eukaryotic promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of direction the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat (LTR), HIV-1 LTR, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

Also Contemplated is the use of chimeric promoters. Chimeric promoters are those that have been artificially constructed to include elements from one or more sources, including both natural and artificial DNA segements. These may comprise modification, additions or deletions of known promoters.

By employing a promoter with well-known properties, the level and pattern of expression of the protein of interest following transfection or transformation can be optimized. Further, selection of a promoter that is regulated in response to specific physiologic signals can permit inducible expression of the gene product.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

(ii) Selectable Markers

In certain embodiments of the invention, the cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

(iii) Multigene Constructs and IRES

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

(iv) Host Cells and Delivery of Expression Vectors

Certain examples of prokaryotic hosts are *E. coli* strain RR1, *E. coli* LE392, *E. coli* B, *E. coil* X 1776 (ATCC No.

31537) as well as *E. coli* W3110 (F-, lambda-, prototrophic, ATCC No. 273325); bacilli such as *Bacillus subtilis*; and other enterobacteriaceae such as *Salmonella typhimurium, Serratia marcescens,* and various Pseudomonas species.

One example of a eukaryotic host cell line lacking p53 is the Saos-2 osteosarcoma line (ATCC No. HTB-85). Also, primary mammalian cell cultures, which often contain mutated p53 genes, may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to enter into host cells and express viral genes efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively limited capacity for foreign DNA sequences and have a restricted host spectrum. They can accommodate only up to 8 kb of foreign genetic material but can be readily introduced in a variety of cell lines and laboratory animals (Nicolas and Rubenstein, 1988; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express a polynucleotide that has been cloned therein. In this context, expression does not require that the gene product be synthesized.

The expression vector comprises a genetically engineered form of adenovirus. Knowledge of the genetic organization of adenovirus, a 36 kb, linear, double-stranded DNA virus, allows substitution of large pieces of adenoviral DNA with foreign sequences up to 7 kb (Grunhaus & Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNAs issued from this promoter possess a 5'-tipartite leader (TPL) sequence which makes them preferred mRNAs for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, typically depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the E3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and B3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g, Vero cells or other monkey embryonic mesenchymal or epithelial cells. As stated above, the preferred helper cell line is 293.

Recently, Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) are employed as follows. A cell inoculum, resuspended in 5 ml of medium, is added to the carrier (50 ml) in a 250 ml Erlenmeyer flask and left stationary, with occasional agitation, for 1 to 4 hours. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 hours.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al., (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact packaging sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al., recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), DNA-loaded polymers, DNA-loaded polymer-:lipid complexes, and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al, 1989). In other embodiments, the liposome may be complexed or employed in conjunction with nuclear non-histone chromosomal proteins (HMG-1) (Kato et al, 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et aL, (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

IV. Screening for Activated p53 Molecules

As stated above, wild-type p53 is known to bind to DNA through a sequence-specific mechanism. This activity is allosterically regulated, as the unmodified polypeptide is inactive until the C-terminal 30 amino acids are bound by antibody, phosphorylated or deleted (Hupp et al., 1992). A model has been formulated in which the unmodified C-terminal tail binds an unidentified peptide binding pocket and holds the p53 tetramer in an inactive conformation (Hupp et al., 1995). The present invention involves the utilization of a high throughput method for generating, screening and isolating mutants of p53 that are constitutively activated.

First, a host cell that does not express p53 is provided. In a preferred embodiment, this cell is a bacterium, for example, E. coli. The full-length p53 cDNA is randomly mutated by mutagenic PCR™ (Cadwell and Joyce, 1992), chemical mutageneis, or other means and transformed into the host cells. Following development of colonies, and optionally after inducement if the p53 gene is under the control of an inducible promoter, colonies are lifted onto nitrocellulose and lysed. The filter-bound library is screened for DNA binding activity, using labeled nucleotide probes, and activity greater than that observed with wild-type p53 is used to identify an activated mutant p53. The mutants that are reproducibly more active than the wild-type are sequenced. The general scheme for this assay is illustrated in FIG. 1.

Mutations conferring activated status on p53 can occur throughout the molecule, as illustrated in FIG. 2B. Mutations within the DNA binding domain (residues 97 to 292) appear to cluster between about residues 106 to 160 and at about residue 268. These thermostable mutations would therefore have been difficult to discover by other means, such as site-directed mutagensis or random mutation of a delimited region. By recombining these mutations into a single molecule, the activity may further be increased.

V. Screening for Thermostable p53 Molecules

Figure 3:
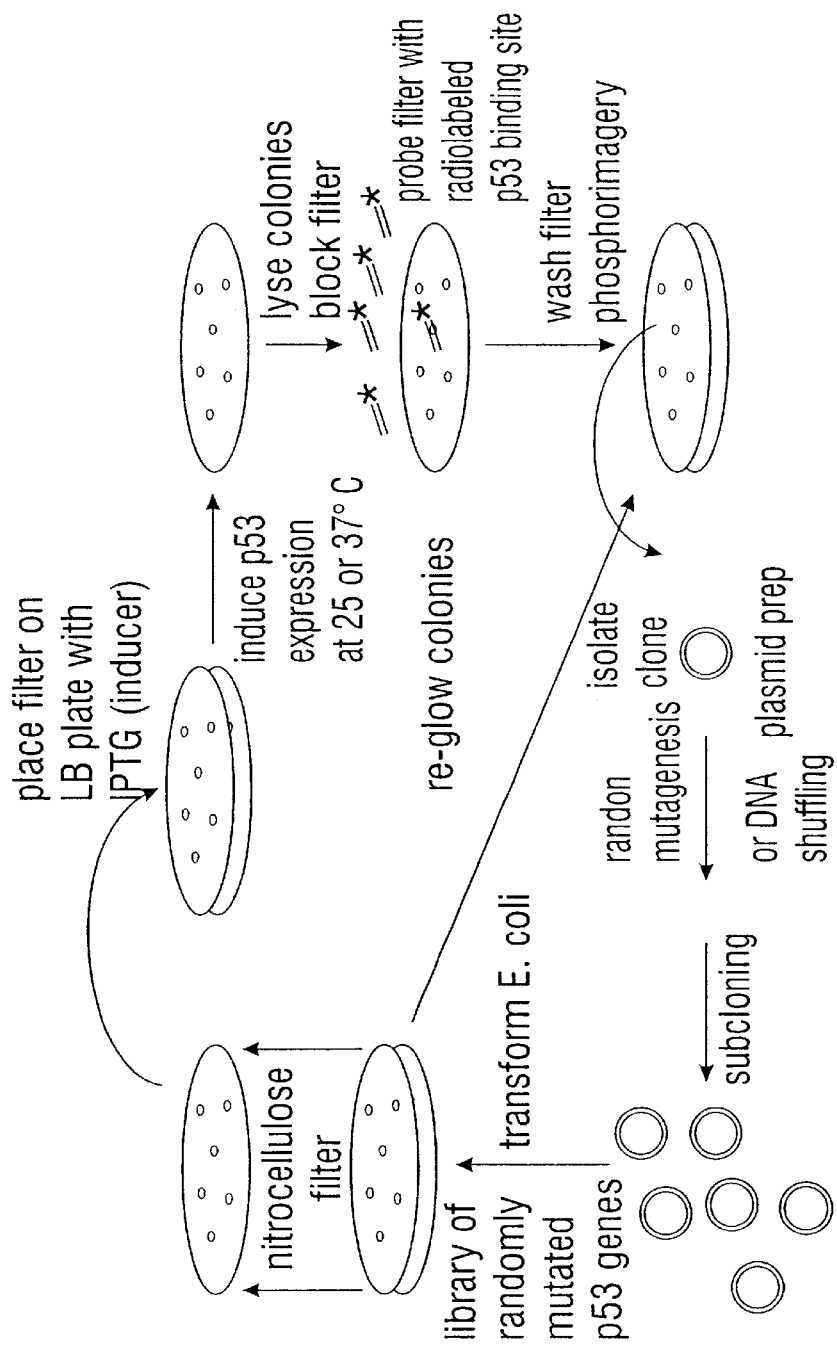
FIG. 3—Scheme for Selection of Thermostable Mutants of p53.
Figure 4:
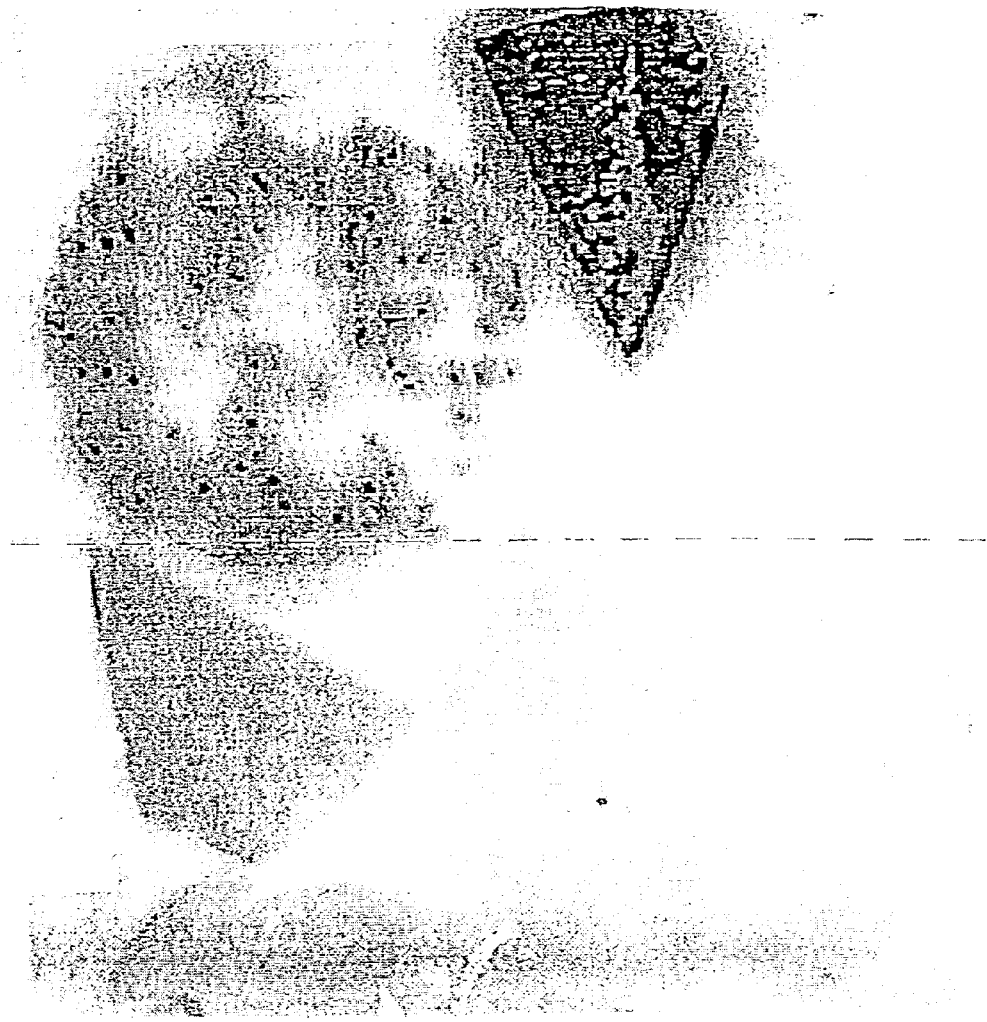
FIG. 4—Screening for Thermostable Mutants. The parental p53Δ30 protein binds to the ligand if the gene is induced at room temperature (top middle), but not if it is induced at 37° C. (bottom left). Some mutant p53Δ30 proteins retain DNA binding activity under permissive conditions (top left), but only a few do so under selective conditions (bottom right). The latter exhibit activity that is reproducibly more thermostable than the parental allele.

The inventors have developed a scheme for identifying p53 variants that are themostable (FIG. 3) similar to that described above. The constitutively active p53 protein (p53Δ30) that lacks the terminal 30 amino acids is overexpressed in E. coli, colonies transferred to a nitrocellulose filter, and the filter probed with a radiolabeled p53 binding site. When the expression construct is induced by IPTG (the relevant promoter being the lacZ promoter) at room temperature, specific interactions between p53Δ30 and its binding sites are observed. However, when the expression construct is induced for two hours at room temperature, followed by two hours at 37° C., no binding activity is detected (FIG. 4). These results confirm that the p53 protein is not stable at 37° C., as has previously been observed by other authors. Such thermolability may well constitute a limitation in current p53 gene therapies.

In order to generate heat resistant p53 variants, random mutations are introduced into p53Δ30 (or any other activated p53 gene) by, for example, mutagenic PCR™, and the protein variants expressed in E. coli under temperature stringent (37° C.) conditions. In one experiment, thirteen of ten thousand colonies exhibited a reproducibly heat resistant phenotype. Mutations in resistant clones can then be "shuffled" together, i.e., artificially recombined, and a second round of expression and screening carried out. Two thousand recombinants were screened for DNA binding activity after a 12 h incubation at 37° C. Three clones were found to reproducibly exhibit greater activity than the most thermostable mutant from the first round of screening.

Notably, for variants selected from the first and second rounds of screening, many of the sequence substitutions map to portions of the p53 structure that are not immediately adjacent to the DNA binding interface. These thermostable mutations would therefore have been difficult to discover by other means, such as site-directed mutagenesis or random mutation of a delimited region. The inventors are in the process of identifying additional variants that confer additional thermostabilities. Combinatorial shuffling may further improve the thermostability of these molecules.

The inventors will clone the genes encoding thermostable p53 variants into eukaryotic expression vectors and assess the stable DNA-binding phenotype, initially observed in bacteria, in mammalian tissue culture cells. In addition, the function of thermostable p53 variants will be examined by co-transfecting expression constructs with a plasmid in which a reporter gene is driven by a p53-dependent promoter. It is anticipated that the thermostable p53 variants will turn over much less quickly than wild-type p53, and thus should produce a larger and longer-lasting signal from the reporter gene. Such p53 mutants may well constitute an improved gene therapeutic.

While the present invention exemplifies selection at 37° C., which is a highly relevant temperature for human in vivo considerations, higher temperatures may be used for selection. Higher temperatures may advantageously be applied to second generation p53 mutation procedures, i.e., those procedures starting with a 37° C. thermostable p53 gene that is mutagenized and selected at a higher temperature (e.g., 38° C. 39° C., 40° C., 41° C., 42° C., 45° C. or 50° C.). Though physiologic temperatures rarely or never reach these extremes, selection under more stringent conditions may improve activity at physiologic temperatures.

VI. Screening for p53 Activators and Inhibitors

In a further variation on the foregoing screens, a screening assay for activators and inhibitors of p53 is provided. It is well known that proteins interact with p53. These include SV40 Large T antigen, heat shock protein 70, Mdm-2, E1b, replicating protein antigen (RPA), xeroderma pigmentosum group B DNA helicase, TATA binding protein and hepatitis B viral X protein.

In order to identify other polypeptides that inhibit or activate p53, a similar high throughput assay as described above is utilized. In a first embodiment, the full length wild-type p53 protein is co-expressed in a bacterial cell along with a single member of a cDNA library derived from quiescent, non-cancerous cells. Following expression, with or without induction as the case may be, cells are screened for DNA binding activity. Any colony exhibiting sequence specific binding activity will be identified, and the cDNA sequence determined.

In the converse of the activator experiment described above, polypeptides that inhibit p53 DNA-binding also will be identified. The activated p53Δ30 gene, which lacks the carboxy-terminal 30 amino acids, is co-expressed in a bacterial host cell with a one member of a cDNA library derived from tumor cells having wild-type p53 genes, which are likely to have repressor or inhibitor genes. Colonies will be probed, as above, with DNA's encoding p53 recognition sites. Absence of DNA binding activity will indicate the presence of an inhibitor, and cDNAs from colonies exhibiting the lack of such activity will be isolated and sequenced.

VII. Screening for Oncogene- and Virus-Resistant p53 Molecules and Viral Inhibitors of p53 Function In yet another embodiment, the present invention provides screening methods that identify p53 polypeptides which are resistant to the inhibitory effects of oncogenes and viral proteins. Examples of inhibitory viral proteins are the SV40 large T antigen and adenovirus E1b. The MDM2 and HPV E6 genes encode oncogenic proteins that bind and inhibit p53 function.

Utilizing the activated form of p53, genes coding therefor are randomly mutagenzied and co-expressed with SV40 large T antigen or other inhibitory polypeptide. Expression of the umnutagenized, activated form of p53 will result in little or no DNA binding activity given the inhibitory effect of, e.g., SV40 large T antigen, DNA binding activity indicates the existence of a mutation that confers resistance to the inhibitory polypeptide.

An alternative format is where the inhibitors are provided bound to a filter or other matrix. The p53 molecule is then contacted with the filter and binding to the filter determined. Binding can be determined by subsequent antibody reactivity with the filter.

In another embodiment, this assaying can be used to identify viral molecules that inhibit p53 function. Using activated p53 molecules as targets, viral libraries can be screened for molecules which abrogate p53 DNA binding functions in assays similar to those described above.

VIII. Screening for Hypermorphic p53 Molecules

Still another screening assay will involve the selection of p53 mutants which have an increased capacity to direct transcription from p53-dependent promoters. Exemplary promoters which are regulated by p53 are p21, MDM-2, Gadd45, Bax and IGF-BP. One of these promoters will be linked to a reporter gene such as GFP, beta-galactosidase or beta-lactamase and introduced into a host cell that lacks p53. Randomly mutated p53-encoding polynucleotides are introduced into the host cell and their ability to direct expression of the reporter gene assessed. The mutant p53 genes may be cotransfected into the host cells along with the reporter gene and the assay conducted in a transient fashion. Alternatively, the reporter gene may be used to first stably transform the host cell, followed by either transient expression or permanent transformation of the host cell with the mutant p53 polynucleotides. In the case where permanent transformation is desired, a retroviral vector may be utilized, as well as a selectable marker such as neo.

Following transformation, the expression of the reporter gene in individual clones will be assessed. In the embodiment where a fluorescent polypeptide is used, fluorescence activated cell sorting (FACS) may advantageously be employed to identify those clones expressing a higher level of p53-mediated transcriptional activity. Once identified, the p53 genes in the cells of interest will be characterized and the particular modifications determined. Using both site-directed and random shuffling approaches, newly identified mutants will be recombined and resorted in order to further increase the transcriptional activity of the p53 molecules.

In an alternative format utilizing eukaryotic cells, a library of randomly mutated p53 cDNAs will be subcloned into a retroviral vector. The library will be packaged into infectious retroviruses and used to infect a p53 deficient cell line, such as Saos-2, transformed with pRevTet-off, which allows for inducible expression of the p53s, and a reporter (e.g., Green Fluorescent Protein) driven by a p53-dependent promoter. The infected cells will be induced (by removing tetracycline from the growth media) and run through FACS. Cells that exhibit fluorescence will be isolated, and will be assumed to contain a p53 variant with greater activity. This activity may be due to self-activation, greater thermostability or other reasons specific to the environment of mammalian cells.

IX. Methods for Therapy

A. Tumor Therapy

One of the preferred embodiments of the present invention involves the use of p53 to induce cell cycle arrest or apoptosis in cancer cells. Target cancer cells include cancers of the lung, brain, prostate, kidney, liver, ovary, breast, skin, stomach, esophagus, head & neck, testicles, colon, cervix, lymphatic system and blood. Of particular interest are non-small cell lung carcinomas including squamous cell carcinomas, adenocarcinomas and large cell undifferentiated carcinomas.

(i) Administration

According to the present invention, one may treat the cancer by directly injecting a tumor with a vector encoding any of the p53 molecules discussed herein. Alternatively, the tumor may be infused or perfused with the vector using any suitable delivery vehicle. Circumferential, local or regional administration, with respect to the tumor, also is contemplated. Finally, systemic administration may be performed. Continuous administration also may be applied where appropriate, for example, where a tumor is excised and the tumor bed is treated to eliminate residual, microscopic disease. Delivery via syringe or catherization is preferred. Such continuous perfusion may take place for a period from about 1–2 hours, to about 2–6 hours, to about 6–12 hours, to about 12–24 hours, to about 1–2 days, to about 1–2 weeks or longer following the initiation of treatment. Generally, the dose of the therapeutic composition via continuous perfusion will be equivalent to that given by a single or multiple injections, adjusted over a period of time during which the perfusion occurs.

In certain embodiments, the tumor being treated may not, at least initially, be resectable. Treatments with therapeutic viral constructs may increase the resectability of the tumor due to shrinkage at the margins or by elimination of certain particularly invasive portions. Following treatments, resection may be possible. Additional viral treatments subsequent to resection will serve to eliminate microscopic residual disease at the tumor site.

A typical course of treatment, for a primary tumor or a post-excision tumor bed, will involve multiple doses. Typical primary tumor treatment involves a 6 dose application over a two week period. The two week regimen may be repeated one, two, three, four, five, six or more times. During a course of treatment, the need to complete the planned dosings may be reevaluated.

(ii) A Clinical Protocol

A particular clinical protocol has been developed to facilitate the treatment of cancer using adenoviral constructs encoding p53. In accordance with this protocol, patients having histologic proof of cancer will be selected. Patients may, but need not have received previous chemo-, radio- or gene therapies. Optimally, patients will have adequate bone marrow function (defined as peripheral absolute granulocyte count of >2,000/mm$^3$ and platelet count of 100,000/mm$^3$), adequate liver function (bilirubin $\leq$1.5 mg/dl) and adequate renal function (creatinine <1.5 mg/dl).

The protocol calls for single dose administration, via intratumoral injection, of a pharmaceutical composition containing between $10^6$ and $10^{13}$ infectious particles of a p53 adenovirus expression construct. For tumors of $\geq$4 cm, the volume administered will be about 4–100 ml (preferably 10 ml, although higher amounts may be utilized for larger tumors), while for tumors <4 cm, a volume of 1–3 ml will be used (preferably 3 ml). Multiple injections will be delivered for a single dose, in 0.1–0.5 ml volumes, with spacing of approximately 1 cm or more.

The treatment course consists of about six doses, delivered over two weeks. Upon election by the clinician, the regimen may be continued, six doses each two weeks, or on a less frequent (monthly, bimonthly, quarterly, etc.) basis.

Where patients are eligible for surgical resection, the tumor will be treated as described above for at least two consecutive two-week treatment courses. Within one week of completion of the second (or more, e.g., third, fourth, fifth, sixth, seventh, eighth, etc.) course, the patient will receive surgical resection. Prior to close of the incision, 10 ml of a pharmaceutical composition containing the p53 adenovirus expression construct ($10^6$–$10^{13}$ infectious particles) will be delivered to the surgical site (operative bed) and allowed to remain in contact for at least 60 minutes. The wound is closed and a drain or catheter placed therein. On the third post-operative day, additional 10 ml of the pharmaceutical composition is administered via the drain and allowed to remain in contact with the operative bed for at least two hours. Removal by suction is then performed, and the drain removed at a clinically appropriate time.

(iii) Combination Therapies

Cancer therapies also include a variety of combination therapies with both chemical and radiation based treatments. Combination chemotherapies include, for example, cisplatin (CDDP), carboplatin, procarbazine, mechlorethamine, cyclophosphamide, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate.

Combination radiation therapies may be x- and γ-irradiation. Dosage ranges for x-irradiation range from daily doses of 2000 to 6000 roentgens for prolonged periods of time (3 to 4 weeks), to single doses of 2000 to 6000 roentgens. Dosages for radioisotopes vary widely, and depend on the half-life of the isotope, the strength and type of radiation emitted, and the uptake by neoplastic cells.

Various combinations may be employed, gene therapy is "A" and the radio- or chemotherapeutic agent is "B":

A/B/A B/A/B B/B/A A/A/B A/B/B B/A/A A/B/B/B B/A/ B/B B/B/B/A B/B/A/B A/A/B/B A/B/A/B A/B/B/A B/B/A/A B/A/B/A B/A/A/B A/A/A/B B/A/A/A A/B/ A/A A/A/B/A

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

B. Anti-HIV Therapy

According to the present invention, HIV-1 or HIV-2 infected cells may be treated with a vector expressing a cleaveable p53 molecule. As discussed above, in one embodiment, the present invention involves the creation of novel p53 polypeptides which are susceptible to cleavage, and hence activation, by the HIV-1 protease molecule. These molecules include protease cleavage sites near the carboxy-terminus of the molecule and, more preferably, at about 30 residues from the carboxy-terminus. Cleavage of this portion of the molecule results in activation of the molecule's DNA binding activity.

In another embodiment, the present invention may be utilized to increase the efficacy of existing HIV therapies. Other therapies suitable for combination with the present invention include AZT treatment and high active anti-retroviral therapy (HAART) which combines the effects of nucleoside reverse transcriptase inhibitors and protease inhibitors, although the latter should not be conducted simultaneously with the present therapy given its reliance on protease activity.

C. Pharmaceutical Compositions and Routes of Administration

Where clinical application of an active ingredient (drugs, polypeptides, antibodies or liposomes containing polynucleotides or expression vectors) is undertaken, it will be necessary to prepare a pharmaceutical composition appropriate for the intended application. Generally, this will entail preparing a pharmaceutical composition that is essentially free of pyrogens, as well as any other impurities that could be harmful to humans or animals. One also will generally desire to employ appropriate buffers to render the complex stable and allow for uptake by target cells.

Aqueous compositions of the present invention comprise an effective amount of the active ingredient, as discussed above, further dispersed in pharmaceutically acceptable carrier or aqueous medium. Such compositions also are referred to as inocula. The phrases "pharmaceutically or pharmacologically acceptable" refer to compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients also can be incorporated into the compositions.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, a controlled release patch, salve or spray.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal or topical. Alternatively, administration will be by orthotopic, intradermal subcutaneous, intramuscular, intraperitoneal, intravenous or intratumoral injection. Such compositions would normally be administered as pharmaceutically acceptable compositions that include physiologically acceptable carriers, buffers or other excipients. A preferred embodiment delivery route, for the treatment of a disseminated disease state is systemic, however, regional delivery is also contemplated.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting dose include physical and clinical state of the patient, the route of administration, the intended goal of treatment and the potency, stability and toxicity of the particular therapeutic substance.

X. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Screens for Thermostable p53 Molecules

Development of screen. The human p53 cDNA gene except for those nucleotides coding for the C-termiinal 30 amino acids (p53Δ30) was amplified by the polymerase chain reaction (PCR™) and subcloned into the prokaryotic expression vector pET20b(+) (Novagen, Madison, Wis.). $E.$ $coli$ strain BL21(DE3) carrying the T7 lysozyme expression vector, pLysS, was transformed with the p53Δ30 expression construct and plated on Luria broth plates containing 34 micrograms/mL chloramphenicol and 100 micrograms/mL ampicillin (LB-chl/amp). After 16 h of growth at 37° C., the colonies were overlaid with a nitrocellulose filter and transferred to LB-chl/amp plates containing 0.5 mM IPTG to induce expression of p53Δ30. The cells remaining on the original plate were re-grown into full colonies by a further 8 h incubation at 37° C. (FIG. 3).

The colonies adsorbed to the nitrocellulose filter were induced at room temperature for four h. Their membranes were disrupted with chloroform gas, giving the intracellular T7 lysozyme access to the peptidoglycan. The filters were treated with DNase I, blocked with milk protein, washed and probed with a radiolabelled palindromic (double-stranded) oligonucleotide that encodes the p53 binding site, p53CON (Funk et al., 1992). The filters were washed again and the quantity of probe bound to each filter was detected by phosphorimagery (Molecular Dynamics). Only colonies containing the p53Δ30 expression vector were bound by the probe (FIG. 4). When the p53Δ30 gene was induced for two h at room temperature, followed by two hours at 37° C., the colonies bound an undetectable quantity of probe (FIG. 4). These results suggest that DNA binding activity can be attributed solely to the p53Δ30 protein, and that this protein is not stable at 37° C. as previously shown by Hansen et al. (1996).

Figure 5:
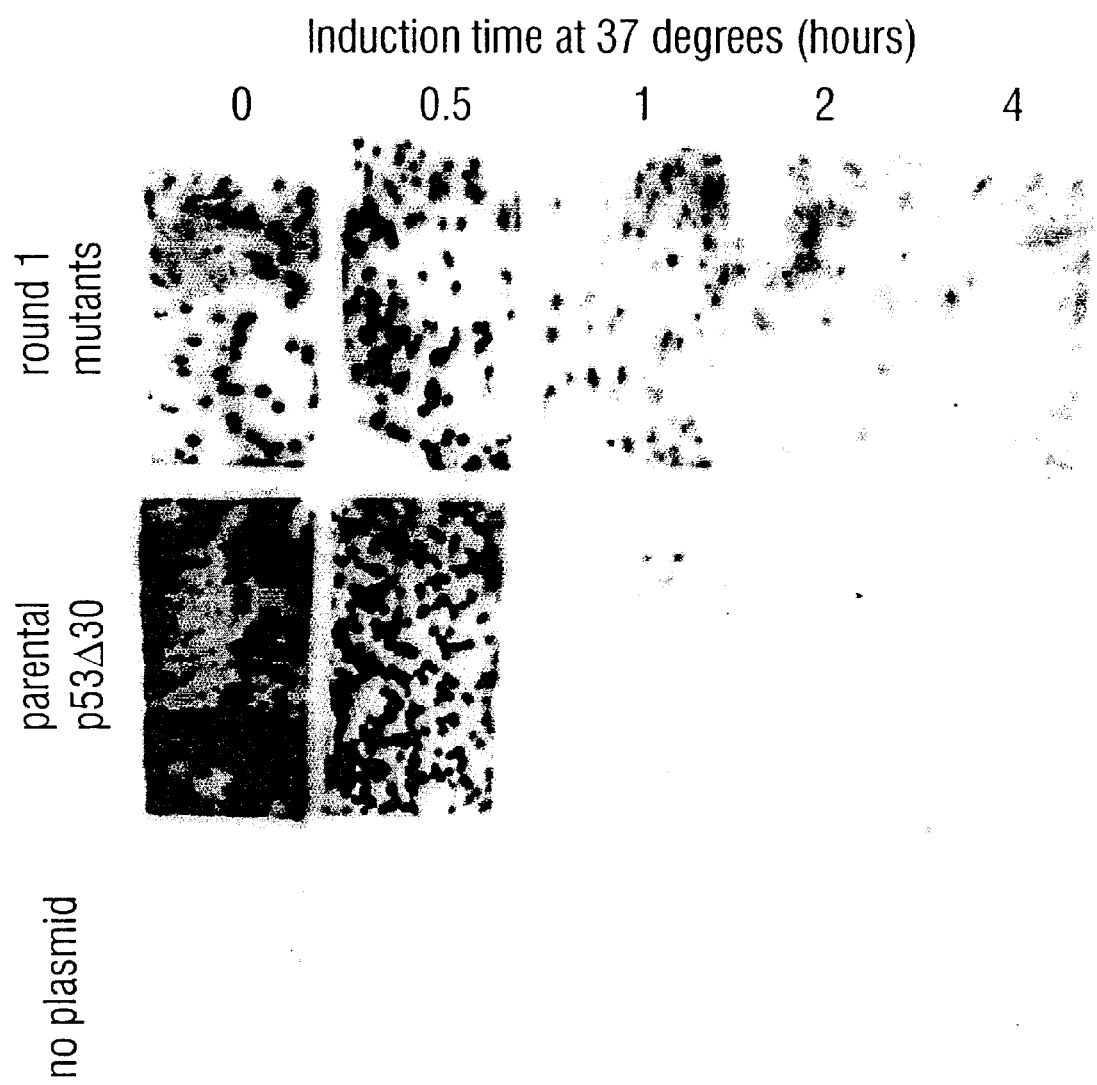
FIG. 5—Denaturation Kinetics of First Round Thermostable Mutants. E. coli expressing a pool of round 1 mutants (top), the parent p53Δ30 allele (middle) or no p53 (bottom) were induced at room temperature and shifted to 37° C. for a total of four hours. The temperature sensitivity of the mutant phenotypes suggest that they are thermostable rather than overexpressed.

Screen for thermostable mutants. Random mutations were introduced into the p53Δ30 gene by mutagenic PCR™ (Cadwell and Joyce, 1992), subcloned back into the expression vector and transformed into $E.$ $coli$ strain BL21(DE3)/pLysS. Ten thousand colonies were plated and induced at room temperature for two h and two more h at 37° C. Those colonies that retained DNA binding activity were picked, re-plated, induced under selective conditions and probed. Thirteen of those colonies exhibited reproducibly greater binding activity than those of the parental strain. The mutant proteins do not exhibit greater activity than the parental p53Δ30 under non-selective conditions (FIG. 5). The simplest explanation of the temperature-dependence of the mutant phenotype is that the mutations confer thermostability.

In vitro recombination. The thirteen mutant p53Δ30 genes were randomly recombined by a recently developed technique called DNA shuffling (Stemmer, 1994). Two thousand recombinants were screened for DNA binding activity after a 12 h incubation at 37° C. Three clones were found to reproducibly exhibit greater activity than the most thermostable mutant from the first round of screening.

Sequencing. The mutant p53Δ30 genes were subcloned and sequenced; the inferred amino acid changes are shown in Table 2. Some of the changes, including those in the most thermostable mutants, were isolated more than once. The mutations do not cluster in any part of the protein. The mechanism by which these mutations enhance thermostability is not obvious. It is therefore unlikely that they could have been identified through rational protein engineering.

Figure 6:
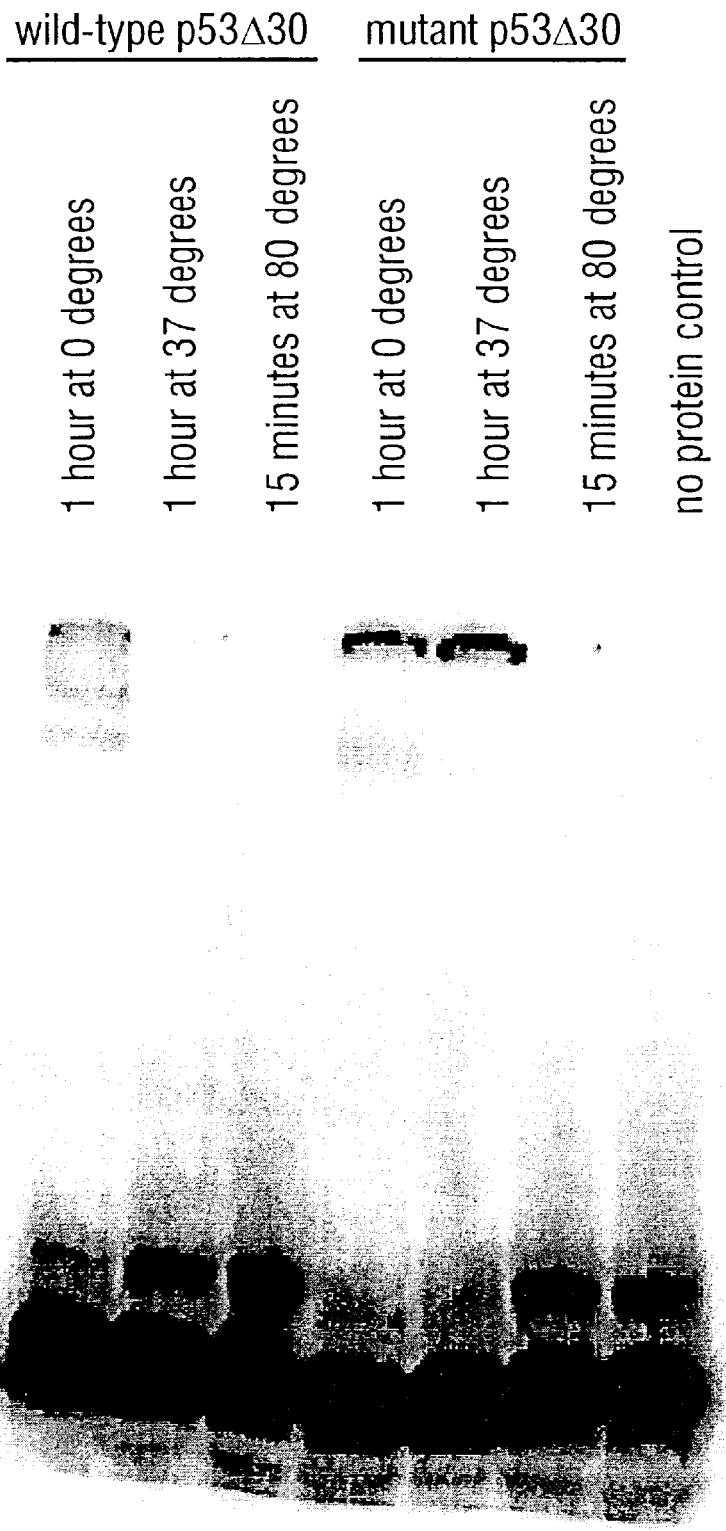
FIG. 6—Purified Mutant p53Δ30 is More Stable than the Parental p53Δ30. Band shift assay showing wild-type and mutant forms of p53Δ30 binding to DNA target at 0° C., 37° C. or 80° C. Upper band reflects DNA bound to p53, while lower band reflects unbound DNA.

In vitro characterization. The mutant and parental genes were subcloned into expression vectors so that they are expressed as fusion proteins with a C-terminal five histidine tag. This modification does not affect DNA binding activity of p53Δ30. The fusion proteins have been purified to homogeneity in a single step by metal affinity chromatography. The DNA binding activity of the purified mutant protein is more stable than that of the wild-type (FIG. 6). The denaturation kinetics of the purified parental and mutant p53Δ30 fusion proteins are presently determined.

E. coli does not modify heterologously expressed p53 (Hupp and Lane, 1994), so the inventors have no reason to suspect that the increased thermostability of the mutant proteins is caused by any temperature-dependent post-translational modifications specific to E. coli. The inventors expect that the mutant p53Δ30 proteins will also prove more soluble and therefore more active in mammalian cells. The most thermostable mutant and parental p53Δ30 cDNAs have been subcloned into the inducible eukaryotic expression vector, pIND (Invitrogen). These expression vectors have been sent to the inventors' collaborator, Prof. Tapas Mukhopadhyay, who will characterize the behavior of these proteins in cultured mammalian cells.

Example 2

Screens for Activated p53 Molecules

Screen for self-activating mutations. The full-length p53 cDNA was randomly mutated by mutagenic PCR™ (Cadwell and Joyce, 1992). The resulting library was screened for mutants with DNA binding activity greater than that of wild-type. The screens were similar to those described above, except that the inductions were carried out at room temperature for two hours (FIG. 2A). The mutants that were reproducibly more active than the wild-type were sequenced. The inferred amino acid changes occur over the whole gene (FIG. 2B). The mutations in the sequence specific DNA binding domain clustered in two areas—that portion of the molecule interacting with the polynucleotide backbone, and a region on the opposite side of the molecule.

Example 3 p53 Molecules for Anti-HIV Therapy

Expression of the wild-type p53 protein normally leads to repression of transcription from the HIV-1 LTR, and inhibition of viral replication. Not surprisingly, this adaptable virus has overcome p53-mediated repression by expressing its own protein, Tat, which represses transcription of p53.

According to the present invention, the inventors have engineered a variant of p53 that can be activated by HIV-1 protease, but is inactive in cells which are not infected by the virus. This approach has several advantages over current therapies. First, it is unlikely that a naturally occurring protein such as p53 will cause unwanted side effects, e.g., immunologic reaction. Second, p53 leads to pleiotropic effects (repression of viral transcription, G1 growth arrest, apoptosis) mediated by cellular factors that inhibit viral replication. This makes it unlike that HIV-1 could evolve immunity against the engineered p53. Third, the p53 variant can serve "double duty" as gene therapy for opportunistic AIDS-associated cancers.

Human p53 cDNA was altered by site-directed mutagenesis so that the HIV-1 protease cleavage site was inserted upstream of the carboxy terminal regulatory domain. The relevant sequences are:

Wild-type p53:
 KDAQAGKEPGGSRAHSSHLK-
  SKKGQSTSRHKKLMFKTEGPDSD (SEQ ID NO:3)
TAT Protease Recognition Site:
 VSFNFPQITL (SEQ ID NO:4)
Modified P53
 KDAQAGKEPGVSFNFPQITLK-
  SKKGQSTSRHKKLMFKTEGPDSD (SEQ ID NO:5)

Wild-type and variant p53 genes were expressed as amino-terminal his-tagged fusion proteins in bacteria, either alone or co-expressed with HIV-1 protease. The bacteria were lysed, and the p53 fusion proteins were purified by nickel chelate affinity chromatography and analyzed by SDS-PAGE (FIG. 7). The mutagenized p53 migrated more quickly than the wild-type protein (as did p53Δ30), but only after coexpression with HIV-1 protease.

Next, the ability of HIV-1 protease-mediated cleaved mutant p53 to bind DNA was tested. Purified proteins were incubated with radiolabeled oligonucleotides that encode the p53 binding site from the p21 enhancer. The bound and free oligonucleotides were separated by electrophoresis and analyzed on a Phosphorimager (FIG. 2). The mutated protein exhibited greatly enhanced DNA binding activity, but only after coexpression with HIV-1 protease. This demonstrates that allosteric regulation by HIV can be engineered into p53.

All of the compositions and disclosed and claimed herein can be made and executed without undue experimentation in light of the present disclosure. While the compositions and methods of this invention have been described in terms of preferred embodiments, it will be apparent to those of skill in the art that variations may be applied to the compositions and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

X. REFERENCES

The following references, to the extent that they provide exemplary procedural or other details supplementary to those set forth herein, are specifically incorporated herein by reference.

Baichwal and Sugden, In: *Gene Transfer*, Kucherlapati R, ed., New York, Plenum Press, 117–148, 1986.
Benvenisty and Neshif, *Proc. Nat'l Acad. Sci. USA*, 83:9551–9555, 1986.

Cadwell and Joyce, *PCR Methods Appl.*, 2(1):28–33, 1992.
Chang et al., *Hepatology*, 14:124A, 1991.
Chen and Okayama, *Mol. Cell Biol.*, 7:2745–2752, 1987.
Coffin, In: Fields B N, Knipe D M, ed. Virology. New York: Raven Press, pp. 1437–1500, 1990.
Couch et al., *Am. Rev. Resp. Dis.*, 88:394–403, 1963.
Couparet al., *Gene*, 68:1–10, 1988.
*Current Protocols in Molecular Biology* (1995)
Dubensky et al., *Proc. Nat'l Acad. Sci. USA*, 81:7529–7533, 1984.
Fechheimer et al, *Proc. Nat'l. Acad. Sci. USA*, 84:8463–8467, 1987.
Ferkol et al., *FASEB J.*, 7:1081–1091, 1993.
Fraley et al., *Proc. Nat'l Acad. Sci. USA*, 76:3348–3352, 1979.
Freshner, In *Animal Cell Culture: a Practical Approach* Second Edition, Oxford/New York, IRL Press, Oxford University Press, 1992.
Friedmann, *Science*, 244:1275–1281, 1989.
Funk et al., *Mol. Cell Biol.*, 12:2866–2871, 1992.
Ghosh-Choudhury et al., *EMBO J.*, 6:1733–1739, 1987.
Ghosh and Bachhawat, (Wu G, Wu C ed.), New York: Marcel Dekker, pp. 87–104, 1991.
Gomez-Foix et al., *J. Biol. Chem.*, 267:25129–25134, 1992.
Gopal, *Mol. Cell Biol.*, 5:1188–1190, 1985.
Graham and Prevec, *Biotechnology*, 20:363–390, 1992.
Graham and Prevec, In: E. J. Murray (ed.), Methods in Molecular Biology: Gene Transfer and Expression Protocol, Clifton, N.J. Humana Press, 7:109–128, 1991.
Graham and Van Der Eb, *Virology*, 52:456–467, 1973.
Graham et al., *J. Gen. Virol.*, 36:59–72, 1977.
Grunhaus and Horwitz, *Seminar in Virology*, 3:237–252, 1992.
Hansen et al., *J. Biol. Chem.*, 271(7):3917–3924, 1996.
Harland and Weintraub, *J. Cell Biol.*, 101:1094–1099, 1985.
Hermonat and Muzycska, *Proc. Nat'l Acad. Sci. USA*, 81:6466–6470, 1984.
Hersdorffer et al., *DNA Cell Biol.*, 9:713–723, 1990.
Herz and Gerard, *Proc. Nat'l Acad. Sci. USA*, 90:2812–2816, 1993.
Hollstein et al., *Science*, 253:49–53, 1991.
Horwich, et al., *J. Virol.*, 64:642–650, 1990.
Hupp and Lane, *Curr. Biol.*, 4(10):865–875, 1994.
Hupp et al., *Cell*; 71(5): 875–886, 1992
Hupp et al., *J Biol Chem.* 1995 Jul 28; 270(30): 18165–18174, 1995.
Hupp et al., *Cell*; 83(2): 237–245, 1995.
Inouye et al., *Nucleic Acids Res.*, 13:3101–3109, 1985.
Jones and Shenk, *Cell*, 13:181–188, 1978.
Kaneda et al., *Science*, 243:375–378, 1989.
Karlsson et al., *EMBO J.*, 5:2377–2385, 1986.
Kato et al., *J. Biol. Chem.*, 266:3361–3364, 1991.
Klein et al., *Nature*, 327:70–73, 1987.
Le Gal La Salle et al., *Science*, 259:988–990, 1993.
Levrero et al., *Gene*, 101:195–202, 1991.
Macejak and Sarnow, *Nature*, 353:90–94, 1991.
Mann et al., *Cell*, 33:153–159, 1983.
Markowitz et al., *J. Virol.*, 62:1120–1124, 1988.
Mulligan, *Science*, 260:926–932, 1993.
Myers, EPO 0273085.
Nicolas and Rubenstein, In: *Vectors: A survey of molecular cloning vectors and their uses.* Rodriguez and Denhardt (eds.), Stoneham: Butterworth, pp. 494–513, 1988.
Nicolau and Sene, *Biochem. Biophys. Acta*, 721:185–190, 1982.
Nicolau et al., *Methods Enzymol.*, 149:157–176, 1987.
Paskind et al., *Virology*, 67:242–248, 1975.
Pelletier and Sonenberg, *Nature*, 334:320–325, 1988.
Perales et al., *Proc. Nat'l Acad. Sci.*, 91:4086–4090, 1994.
Potter et al., *Proc. Nat'l Acad. Sci. USA*, 81:7161–7165, 1984.
Racher et al., *Biotechnology Techniques*, 9:169–174, 1995.
Ragot et al., *Nature*, 361:647–650, 1993.
Renan, *Radiother. Oncol.*, 19:197–218, 1990.
Rich et al., *Hum. Gene Ther.*, 4:461–476, 1993.
Ridgeway, In: Rodriguez R L, Denhardt D T, ed. Vectors: A survey of molecular cloning vectors and their uses. Stoneham: Butterworth, pp.467–492, 1988.
Rippe et al., *Mol. Cell Biol.*, 10:689–695, 1990.
Rosenfeld et al., *Science*, 252:431–434, 1991.
Rosenfeld et al., *Cell*, 68:143–155, 1992.
Roux et al., *Proc. Nat'l Acad. Sci. USA*, 86;9079–9083, 1989.
Stemmer, *Proc. Nat'l Acad. Sci. USA*, 91:10747–10751, 1994.
Stratford-Perricaudet and Perricaudet, In: *Human Gene Transfer*, Eds, O. Cohen-Haguenauer and M. Boiron, Editions John Libbey Eurotext, France, pp. 51–61, 1991.
Stratford-Perricaudet et al., *Hum. Gene Ther.*, 1:241–256, 1990.
Temin, In: *Gene Transfer*, Kucherlapati (ed.), New York: Plenum Press, pp. 149–188, 1986.
Top et al., *J. Infect. Dis.*, 124:155–160, 1971.
Tur-Kaspa et al., *Mol. Cell Biol.*, 6:716–718, 1986.
U.S. Pat. No. 4,888,286
Varmus et al., *Cell*, 25:23–36, 1981.
Wagner et al., *Proc. Nat'l Acad. Sci.*, 87(9):3410–3414, 1990.
Weinberg, *Science*, 254:1138–1145, 1991.
Wong et al., *Gene*, 10:87–94, 1980.
Wu & Wu, Biochemistry, 27;887–892, 1988.
Wu & Wu, *J. Biol. Chem.*, 262:4429–4432, 1987.
Wu and Wu, *Adv. Drug Delivery Rev.*, 12:159–167, 1993.
Yang et al., *Proc. Nat'l Acad. Sci USA*, 87:9568–9572, 1990.
Zelenin et al., *FEBS Lett.*, 280:94–96, 1991.

What is claimed is:

1. A polynucleotide encoding a thermostable p53 polypeptide comprising a first point mutation selected from the group consisting of $Val^{133}$, $Tyr^{239}$, $Asp^{268}$, $Val^{336}$, $Pro^{364}$, $Val^{62}$, $Thr^{116}$, $Pro^{166}$, $Thr^{270}$, $Ser^{88}$, $Ile^{157}$, $Val^{344}$, $Gly^{42}$, $Ser^{268}$, $Lys^{51}$, $Gly^{326}$, $Glu^{207}$, $Ser^{212}$, $His^{264}$, $Ala^{203}$, $Leu^{80}$, $Ala^{30}$, $Lys^{56}$, $Asn^{106}$, $Arg^{115}$, $Ser^{227}$, $Met^{344}$, $Gln^{45}$, $Ala^{102}$, $Ser^{191}$, $Thr^{322}$, $Ala^{31}$, $Gly^{49}$, $Thr^{183}$, $Ile^{264}$ and $Val^{346}$, wherein the noted amino acid position is in reference to SEQ ID NO:2.

2. The polynucleotide of claim 1, wherein said polynucleotide encodes a polypeptide further comprising a second point mutation.

3. The polynucleotide of claim 1, wherein said first point mutation is $Gly^{42}$ and said second point mutation is $Ser^{268}$, wherein the noted amino acid position is in reference to SEQ ID NO:2.

4. The polynucleotide of claim 1, wherein said first point mutation is $Lys^{51}$ and said second point mutation is $Gly^{326}$, wherein the noted amino acid position is in reference to SEQ ID NO:2.

5. The polynucleotide of claim 1, wherein said first point mutation is $Leu^{80}$ and said second point mutation is $Ala^{203}$, wherein the noted amino acid position is in reference to SEQ ID NO:2.

6. The polynucleotide of claim 1, wherein said first point mutation is $Ser^{277}$ and said second point mutation is $Met^{344}$, wherein the noted amino acid position is in reference to SEQ ID NO:2.

7. The polynucleotide of claim 1, wherein said polynucleotide encodes polypeptide further comprising a third point mutation.

8. The polynucleotide of claim 7, wherein said first point mutation is $Tyr^{239}$, said second point mutation is $Asp^{269}$, and said third point mutation is $Val^{336}$, wherein the noted amino acid position is in reference to SEQ ID NO:2.

9. The polynucleotide of claim 7, wherein said first point mutation is $Val^{62}$, said second point mutation is $Tyr^{239}$, and said third point mutation is $Asp^{268}$, wherein the noted amino acid position is in reference to SEQ ID NO:2.

10. The polynucleotide of claim 7, wherein said first point mutation is $Asp^{268}$, said second point mutation is $Val^{336}$, and said third point mutation is $Pro^{364}$, wherein the noted amino acid position is in reference to SEQ ID NO:2.

11. The polynucleotide of claim 7, wherein said first point mutation is $Ser^{88}$, said second point mutation is $Ile^{157}$, and said third point mutation is $Val^{344}$, wherein the noted amino acid position is in reference to SEQ ID NO:2.

12. The polynucleotide of claim 7, wherein said first point mutation is $Glu^{207}$, said second point mutation is $Ser^{212}$, and said third point mutation is $His^{364}$, wherein the noted amino acid position is in reference to SEQ ID NO:2.

13. The polynucleotide of claim 7, wherein said polynucleotide encodes a polypeptide further comprising a fourth point mutation.

14. The polynucleotide of claim 13, wherein said first point mutation is $Thr^{116}$, said second point mutation is $Pro^{166}$, said third point mutation is $Asp^{268}$, and said fourth point mutation is $Thr^{270}$, wherein the noted amino acid position is in reference to SEQ ID NO:2.

15. The polynucleotide of claim 14, wherein said polynucleotide encodes a polypeptide further comprising a fifth point mutation.

16. The polynucleotide of claim 15, wherein said first point mutation is $Val^{133}$, said second point mutation is $Tyr^{239}$, said third point mutation is $Asp^{268}$, said fourth point mutation is $Val^{336}$, and said fifth point mutation is $Pro^{364}$, wherein the noted amino acid position is in reference to SEQ ID NO:2.

17. The polynucleotide of claim 15, wherein said first point mutation is $Ala^{30}$, said second point mutation is $Lys^{56}$, said third point mutation is $Asn^{106}$, said fourth point mutation is $Arg^{115}$, and said fifth point mutation is $Ala^{203}$, wherein the noted amino acid position is in reference to SEQ ID NO:2.

18. The polynucleotide of claim 15, wherein said first point mutation is $Gln^{45}$, said second point mutation is $Ala^{102}$, said third point mutation is $Ser^{191}$, said fourth point mutation is $Glu^{207}$, and said fifth point mutation is $Thr^{332}$, wherein the noted amino acid position is in reference to SEQ ID NO:2.

19. The polynucleotide of claim 15, wherein said first point mutation is $Ala^{31}$, said second point mutation is $Gly^{49}$, said third point mutation is $Thr^{183}$, said fourth point mutation is $Ile^{264}$, and said fifth point mutation is $Val^{346}$, wherein the noted amino acid position is in reference to SEQ ID NO:2.

* * * * *

SEQUENCE LISTING

<160> NUMBER OF SEQ ID NOS: 5

<210> SEQ ID NO 1
<211> LENGTH: 1288
<212> TYPE: DNA
<213> ORGANISM: Homo sapiens

<400> SEQUENCE: 1

-continued

```
ccacctgaag tccaaaaagg gtcagtctac ctcccgccat aaaaaactca tgttcaagac      60
agaagggcct gactcagact gacattctcc acttcttgtt ccccactgac agcctcccac     120
ccccatctct ccctcccctg ccattttggg ttttgggtct ttgaacccct gcttgcaata    180
ggtgtgcgtc agaagcaccc aggacttcca tttgctttgt cccggggctc cactgaacaa    240
gttggcctgc actggtgttt tgttgtgggg aggaggatgg ggagtaggac ataccagctt    300
agattttaag gttttactg tgagggatgt ttgggagatg taagaaatgt tcttgcagtt    360
aagggttagt ttacaatcag ccacattcta ggtaggggcc cacttcaccg tactaaccag    420
ggaagctgtc cctcactgtt gaattttctc taacttcaag gcccatatct gtgaaatgct    480
ggcatttgca cctacctcac agagtgcatt gtgagggtta atgaaataat gtacatctgg    540
ccttgaaacc acctttttatt acatggggtc tagaacttga ccccttgag ggtgcttgtt    600 ccctctccct gttggtcggt gggttggtag tttctacagt tgggcagctg gttaggtaga    660
gggagttgtc aagtctctgc tggcccagcc aaaccctgtc tgacaacctc ttggtgaacc    720
ttagtaccta aaaggaaatc tcaccccatc ccacaccctg gaggatttca tctcttgtat    780
atgatgatct ggatccacca agacttgttt tatgctcagg gtcaatttct tttttcttt    840 tttttttttt tttctttttc tttgagactg ggtctcgctt tgttgcccag gctggagtgg    900
agtggcgtga tcttggctta ctgcagcctt tgcctcccg gctcgagcag tcctgcctca    960
gcctccggag tagctgggac acaggttca tgccaccatg ccagccaac ttttgcatgt   1020 tttgtagaga tgggtctca cagtgttgcc caggctggtc tcaaactcct gggctcaggc   1080
gatccacctg tctcagcctc ccagagtgct gggattacaa ttgtgagcca ccacgtccag   1140
ctggaagggt caacatcttt tacattctgc aagcacatct gcattttcac cccacccttc   1200
ccctccttct ccctttttat atcccatttt tatatcgatc tcttatttta caataaaact   1260
ttgctgccac ctgtgtgtct gagggtg                                        1288
```

<210> SEQ ID NO 2
<211> LENGTH: 393
<212> TYPE: PRT
<213> ORGANISM: Homo sapiens

<400> SEQUENCE: 2

```
Met Glu Glu Pro Gln Ser Asp Pro Ser Val Glu Pro Pro Leu Ser Gln
  1               5                  10                  15

Glu Thr Phe Ser Asp Leu Trp Lys Leu Leu Pro Glu Asn Asn Val Leu
             20                  25                  30

Ser Pro Leu Pro Ser Gln Ala Met Asp Asp Leu Met Leu Ser Pro Asp
         35                  40                  45

Asp Ile Glu Gln Trp Phe Thr Glu Asp Pro Gly Pro Asp Glu Ala Pro
     50                  55                  60

Arg Met Pro Glu Ala Ala Pro Arg Val Ala Pro Gly Pro Ala Ala Pro
 65                  70                  75                  80

Thr Pro Ala Ala Pro Ala Pro Ala Pro Ser Trp Pro Leu Ser Ser Ser
                 85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140
```

-continued

```
Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Cys
            165                 170                 175

Pro His His Glu Arg Cys Ser Asp Ser Asp Gly Leu Ala Pro Pro Gln
        180                 185                 190

His Leu Ile Arg Val Glu Gly Asn Leu Arg Val Glu Tyr Leu Asp Asp
    195                 200                 205

Arg Asn Thr Phe Arg His Ser Val Val Pro Tyr Glu Pro Pro Glu
210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
                260                 265                 270

Arg Val Cys Ala Cys Pro Gly Arg Asp Arg Arg Thr Glu Glu Glu Asn
            275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
                340                 345                 350

Ala Gln Ala Gly Lys Glu Pro Gly Gly Ser Arg Ala His Ser Ser His
            355                 360                 365

Leu Lys Ser Lys Gly Gln Ser Thr Ser Arg His Lys Lys Leu Met
    370                 375                 380

Phe Lys Thr Glu Gly Pro Asp Ser Asp
385                 390

<210> SEQ ID NO 3
<211> LENGTH: 43
<212> TYPE: PRT
<213> ORGANISM: Homo sapiens

<400> SEQUENCE: 3

Lys Asp Ala Gln Ala Gly Lys Glu Pro Gly Gly Ser Arg Ala His Ser
1               5                   10                  15

Ser His Leu Lys Ser Lys Lys Gly Gln Ser Thr Ser Arg His Lys Lys
            20                  25                  30

Leu Met Phe Lys Thr Glu Gly Pro Asp Ser Asp
        35                  40

<210> SEQ ID NO 4
<211> LENGTH: 10
<212> TYPE: PRT
<213> ORGANISM: Homo sapiens

<400> SEQUENCE: 4

Val Ser Phe Asn Phe Pro Gln Ile Thr Leu
1               5                   10

<210> SEQ ID NO 5
<211> LENGTH: 44
```

-continued

```
<212> TYPE: PRT
<213> ORGANISM: Homo sapiens

<400> SEQUENCE: 5

Lys Asp Ala Gln Ala Gly Lys Glu Pro Gly Val Ser Phe Asn Phe Pro
 1               5                  10                  15

Gln Ile Thr Leu Lys Ser Lys Lys Gly Gln Ser Thr Ser Arg His Lys
                20                  25                  30

Lys Leu Met Phe Lys Thr Glu Gly Pro Asp Ser Asp
             35                  40
```